US008115600B2

(12) United States Patent
Stevenson et al.

(10) Patent No.: US 8,115,600 B2
(45) Date of Patent: Feb. 14, 2012

(54) RFID DETECTION AND IDENTIFICATION SYSTEM INCLUDING AN RFID READER HAVING A LIMITED TRANSMIT TIME AND A TIME-OUT PERIOD TO PROTECT A MEDICAL DEVICE AGAINST RFID-ASSOCIATED ELECTROMAGNETIC INTERFERENCE

(75) Inventors: Robert A. Stevenson, Canyon Country, CA (US); Geddes Frank Owen Tyers, Vancouver (CA); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 405 days.

(21) Appl. No.: 12/566,490

(22) Filed: Sep. 24, 2009

(65) Prior Publication Data
US 2010/0123547 A1    May 20, 2010

Related U.S. Application Data

(60) Provisional application No. 61/116,094, filed on Nov. 19, 2008.

(51) Int. Cl.
*G08B 13/14* (2006.01)
*H04Q 5/22* (2006.01)
*G06K 7/10* (2006.01)
*G01S 13/08* (2006.01)
*H04B 5/00* (2006.01)
(52) U.S. Cl. ............... 340/10.1; 340/572.1; 340/539.11; 235/472.01; 342/51; 455/193.1; 455/41.1; 455/41.2
(58) Field of Classification Search .................. None
See application file for complete search history.

(56) References Cited

U.S. PATENT DOCUMENTS

| | | | |
|---|---|---|---|
| 4,424,551 A | 1/1984 | Stevenson et al. | |
| 4,881,061 A | 11/1989 | Chambers | |
| 5,333,095 A | 7/1994 | Stevenson et al. | |
| 5,905,627 A | 5/1999 | Brendel et al. | |
| 6,002,344 A | 12/1999 | Bandy et al. | |
| 6,040,774 A * | 3/2000 | Schepps ................ | 340/572.1 |
| 6,275,369 B1 | 8/2001 | Stevenson et al. | |
| 6,566,978 B2 | 5/2003 | Stevenson et al. | |
| 6,566,997 B1 | 5/2003 | Bradin | |
| 6,693,539 B2 | 2/2004 | Bowers et al. | |
| 6,765,779 B2 | 7/2004 | Stevenson et al. | |
| 7,046,145 B2 | 5/2006 | Maloney | |

(Continued)

OTHER PUBLICATIONS

David L. Hayes, Paul J. Wang, Dwight W. Reynolds, et al.; Interference with Cardiac Pacemakers by Cellular Telephones; The New England Journal of Medicine; May 22, 1997; pp. 1473-1479, vol. 336, No. 21; Massachusetts Medical Society.

(Continued)

*Primary Examiner* — Jennifer Mehmood
*Assistant Examiner* — Fekadeselassie Girma
(74) *Attorney, Agent, or Firm* — Michael F. Scalise

(57) ABSTRACT

A system is provided for identifying implanted medical devices, leads and systems, as well as objects in close proximity to a patient having an implanted active medical device, using a radio frequency identification (RFID) tag having retrievable information relating to the AIMD, lead system and/or patient. An RFID tag communicator includes a circuit for limiting the total continuous transmit time of an interrogation signal, and a time-out circuit for delaying a second and any subsequent interrogation of the RFID tag.

59 Claims, 34 Drawing Sheets

U.S. PATENT DOCUMENTS

| | | |
|---|---|---|
| 7,073,712 B2 | 7/2006 | Jusas et al. |
| 7,135,963 B2 | 11/2006 | Brillon |
| 7,180,420 B2 | 2/2007 | Maurer |
| 7,382,255 B2 | 6/2008 | Chung |
| 7,411,921 B2 | 8/2008 | Strong et al. |
| 7,456,743 B2 | 11/2008 | Malacarne et al. |
| 7,527,198 B2 | 5/2009 | Salim et al. |
| 7,557,711 B2 | 7/2009 | Volpi et al. |
| 7,557,713 B2 | 7/2009 | Cox |
| 7,595,723 B2 | 9/2009 | Heitzmann et al. |
| 2003/0114104 A1 | 6/2003 | Want et al. |
| 2004/0193453 A1 | 9/2004 | Butterfield et al. |
| 2006/0212096 A1 | 9/2006 | Stevenson |
| 2006/0240771 A1* | 10/2006 | Graves et al. ............ 455/39 |
| 2007/0008113 A1 | 1/2007 | Spoonhower et al. |
| 2007/0017136 A1 | 1/2007 | Mosher, Jr. et al. |
| 2007/0038402 A1 | 2/2007 | Zhang |
| 2007/0229269 A1 | 10/2007 | Morris |
| 2007/0279191 A1* | 12/2007 | Yamamoto et al. .......... 340/10.1 |
| 2008/0048855 A1 | 2/2008 | Berger |

OTHER PUBLICATIONS

Seth J. Seidman, Randall Brockman, Brian March Lewis, et al., "In Vitro Tests Reveal Sample Radio Frequency Identification Readers Including Clinically Significant Electromagnetic Interference to Implantable Pacemakers and Implantable Cardioverter Defibrillators," Hearth Rhythm Journal (accepted but not published yet).

* cited by examiner

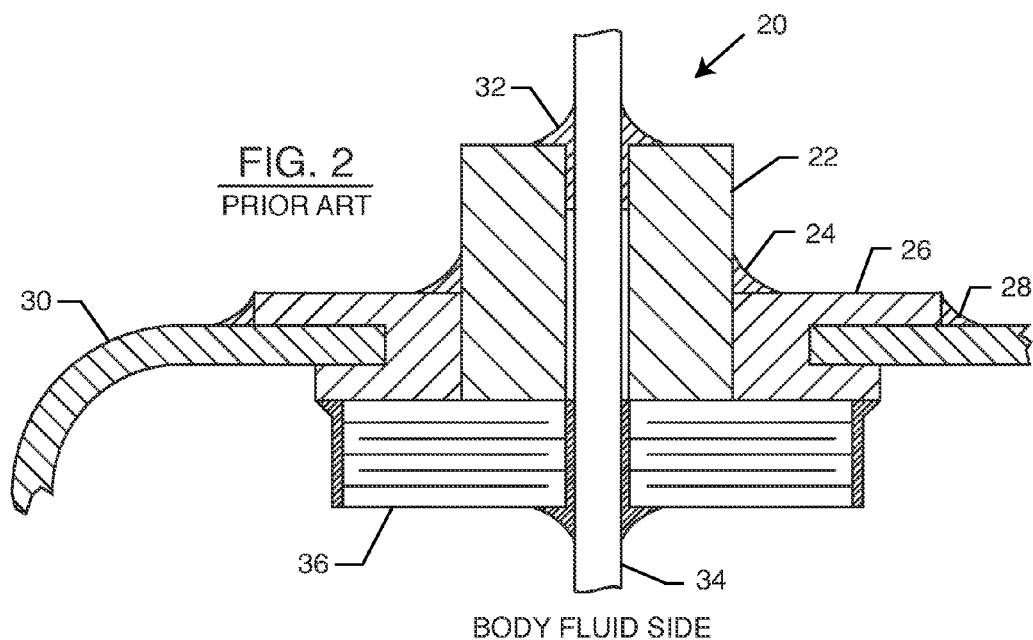
FIG. 2
PRIOR ART
BODY FLUID SIDE
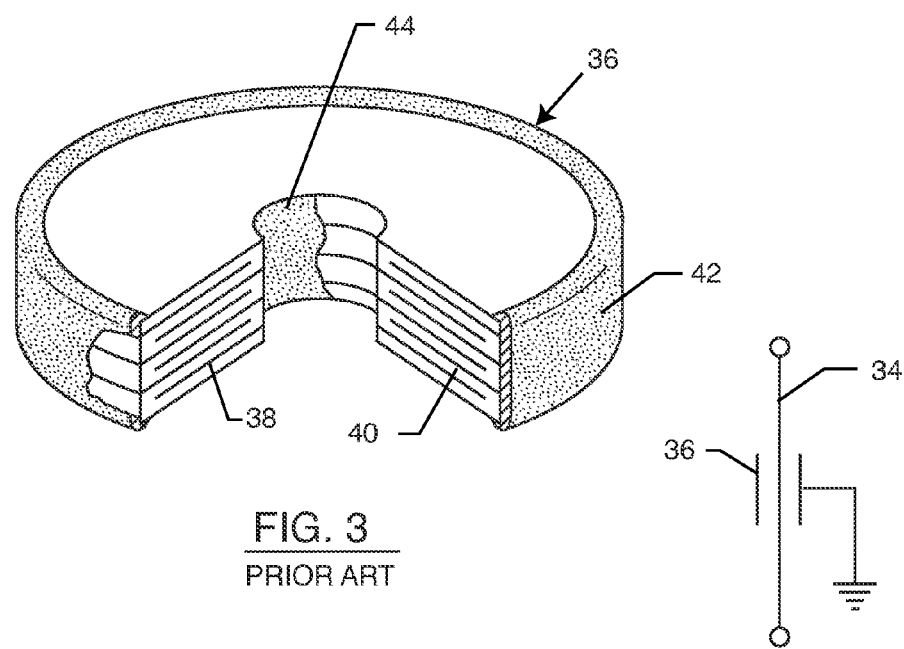
FIG. 3
PRIOR ART
FIG. 4
PRIOR ART RFID Readers Tested by FDA

| RFID Equipment Code | RFID Antenna Configuration (cm) | Governing Standard | Carrier Frequency (MHz) | Max field intensity (A/m Peak @ 2.5 cm | RF Usage |||||
|---|---|---|---|---|---|---|---|---|---|
| | | | | | Pulse Format | Pulse Repetition Rate (Hz) | Duty Factor | Pulse Width (ms) | |
| 1 | Loop 85 x 50 | ISO 11785 | 0.134 | 68 | CW | | | | |
| 2 | Loop 85 x 50 | ISO 11785 | 0.134 | 162 | SEQ | 14.3 | 0.72 | 49.9 | |
| 3 | Loop 20 x 20 | ISO 11785 | 0.134 | 269 | SEQ | 10.7 | 0.54 | 50.3 | |
| 4 | Loop 20 x 20 | ISO 11785 | 0.134 | 267 | SEQ | 7 | 0.69 | 97.8 | |
| 5 | Loop 20 x 20 | ISO 11785 | 0.134 | 258 | SEQ | 25.8 | 0.42 | 16.4 | |
| 6 | Loop 31 x 31 | ISO 18000 3 mode 1 | 13.56 | 4.6 | | 10.9 | 0.11 | 10.3 | |
| 7 | Loop 20 x 20 | ISO 18000 3 mode 1 | 13.56 | 4.9 | | 4 | 0.13 | 31.9 | |
| 8 | Loop 31 x 31 | ISO 18000 3 mode 1 | 13.56 | 8.6 | CW | | | | |
| 9 | Loop 31 x 31 | ISO 18000 3 mode 1 | 13.56 | 8.7 | Full Duplex | 0.9 | 1.0 | 1070 | |
| 10 | Loop 31 x 31 | ISO 18000 3 mode 1 | 13.56 | 8.8 | Full Duplex | 11.1 | 1.0 | 90 | |
| 11 | Handheld | ISO 18000 3 mode 1 | 13.56 | 7.8 | | 3.5 | 0.92 | 264.0 | |
| 12 | XRAY Needed | ISO 18000-6c | 915 | -- | | 56100 | 0.72 | 0.01 | |
| 13 | XRAY Needed | ISO 18000-6c | 915 | -- | | NA | NA | NA | |

FIG. 7

2006 and 2008 FDA TESTS

| 2006 | 2008 |
|---|---|
| • 22 Pacemakers | • 15 Pacemakers |
| • 19 ICDs | • 15 ICDs |
| • 7 RFID Systems | • 13 RFID Systems |
|   - Two 134 kHz Systems |   - Five 134 kHz Systems |
|   - Four 13.56 MHz Systems |   - Six 13.56 MHz Systems |
|   - One 915 MHz Systems |   - Two 915 MHz Systems |

FIG. 8

Maximum Recorded Threshold Distances of Reactions

- Pacemaker
  - Any Reaction
    - 60 cm (occasional atrial and ventricular pacing) LF
    - 22.5 cm (occasional ventricular pacing) HF
  - Class I Reaction (total atrial and ventricular inhibition)
    - 40 cm LF
    - 20 cm HF
- ICD
  - Any Reaction
    - 40 cm (occasional atrial inhibition) LF
    - 22.5 cm (occasional atrial inhibition) HF
  - Class I Reaction (inappropriate high voltage shock)
    - 12.5 cm LF
    - No Class 1 Reactions at HF

FIG. 27

RFID DETECTION AND IDENTIFICATION SYSTEM INCLUDING AN RFID READER HAVING A LIMITED TRANSMIT TIME AND A TIME-OUT PERIOD TO PROTECT A MEDICAL DEVICE AGAINST RFID-ASSOCIATED ELECTROMAGNETIC INTERFERENCE

BACKGROUND OF THE INVENTION

The present invention relates to design modifications to prior art or newly designed RFID interrogation systems for protecting a medical device against RFID-associated electromagnetic interference (EMI). More particularly, the novel RFID interrogation systems include a radio frequency identification (RFID) communicator which has a circuit for limiting the total continuous transmit time of an electromagnetic signal, and a time-out circuit for delaying a subsequent transmission of the electromagnetic signal.

The RFID reader industry has literally been exploding over the last few years with new applications and indications being discovered on what sometimes almost seems a daily basis. For example, RFID readers and their associated tags are being used for inventory tracking, pharmaceutical tracking, tracking of patients in hospitals, automated checkout in super markets of a basket full of goods with associated RFID tags, automobile keyless entry systems and keyless ignition systems, operating room sponge detector systems, and identification of patient RFID wrist bands. There are several main frequency bands that are now dominating the worldwide RFID industry. Four of the popular ones are low frequency (LF) which generally ranges from 125 to 150 kHz, high frequency (HF) which is at 13.56 MHz, very high frequency (VHF) which is at 433 MHz, and ultra high frequency (UHF) which generally operates at 915 MHz. Moreover, there are both national (American) and international standards (ISO) defining the modulation protocols and pulse widths and repetition rates so that standardized RFID tags can be read by a wide variety of readers. In fact, many readers transmit over a broad range of the RFID protocols for this exact reason. With the explosion of RFID emitters (readers also known as interrogators and sometimes referred to herein as communicators), patients with passive or active (electronic) medical devices (PMDs or AMDs) are increasingly running the risk of coming in close contact with such emitters. AMDs can also be implanted inside (or partially inside) the human body and are known as active implantable medical devices (AIMDs).

FIG. 1 is a wire formed diagram of a generic human body. Various locations are shown for active, passive, structural and other implantable and external medical devices 10 that are currently in use, and in which the present invention may find application. 10A represents a family of external and implantable hearing devices which can include the group of hearing aids, cochlear implants, piezoelectric sound bridge transducers and the like. 10B includes an entire variety of neurostimulators and brain stimulators, and hydrocephalic fluid pumps, drug and hormone insulin injection administration devices, etc. Neurostimulators are used, for example, to stimulate the Vagus nerve to treat epilepsy, obesity, Parkinsonism and depression. Brain stimulator systems are similar to a pacemaker-like pulse generator and include leads leading to electrodes implanted deep into the brain. One application involves sensing of the onset of abnormal SNS electrical activity and then providing electrical stimulation to brain tissue to abort the seizure. The electrodes on the end of the leads that arise from a deep brain stimulator are often positioned in the brain tissue using imaging, most commonly during real time MRI. 10C shows a cardiac pacemaker which is well-known in the art. 10D includes the various types of left ventricular assist devices (LVAD's), and artificial hearts, for example, the recently introduced centrifugal empowered devices. 10E includes an entire family of drug pumps which can be used for dispensing of insulin, chemotherapy drugs, pain medications and the like. Insulin pumps are evolving from passive devices to active or semi-active devices that have sensors and closed loop systems wherein real time monitoring of blood sugar levels is associated with directly related and programmable dose responses. These devices tend to be more sensitive to EMI than passive pumps that have no sense circuitry or transcutaneous leads. 10F includes a variety of external or implantable bone growth stimulators for rapid healing of fractures. 10G includes urinary and/or fecal incontinence devices. 10H includes the family of pain relief spinal cord stimulators and anti-tremor stimulators. 10H also includes an entire family of other types of neurostimulators used to block pain. 10I is representative of implantable cardioverter defibrillators (ICDs) including those with biventricular and multi-site synchronization capabilities for the treatment of congestive heart failure (CHF). 10J illustrates an externally worn device. This external pack could be an insulin or other drug pump, an external neurostimulator or pain suppression device, a Holter monitor with skin electrodes or even a ventricular assist device power pack. 10K illustrates the insertion of transcutaneous probe or catheter. These devices can be inserted into the femoral vein, for example, or into many other endovascular or endothelial lined cavities in the human body.

It would be highly undesirable for any type of AIMD to malfunction when exposed to an RFID reader. This includes externally worn AIMDs such as a Holter monitor. It would be very confusing for medical personnel to interrogate the Holter monitor which stores, for example, cardiac electrograms, and see what they thought was a sustained dangerous cardiac arrhythmia which was in fact due to persistent EMI from an RFID interrogation.

It has been demonstrated that RFID communicators, such as RFID readers, interrogators and emitters, can interfere with medical devices such as implanted cardiac pacemakers and implantable cardioverter defibrillators (ICDs). Initial studies conducted by the inventors have been corroborated through two extensive studies at the FDA Center for Devices and Radiological Health (FDA-CDRH). In laboratory studies in 2006 and 2008 at the FDA-CDRH, it was determined that RFID readers can and do cause potentially serious EMI to both cardiac pacemakers and ICDs. The FDA report entitled "In Vitro Tests Reveal Sample Radio Frequency Identification Readers Inducing Clinically Significant Electromagnetic Interference to Implantable Pacemakers and Implantable Cardioverter Defibrillators" is slated to be published in The Heart Rhythm Society journal. The FDA, in its 2008 study, referenced an article published in the New England journal of Medicine on May 27, 1997. This was a seminal paper authored by Dr. David Hayes, et al. where the possible types of responses to EMI of both pacemakers and ICDs were analyzed and classified. The paper classified the EMI responses into a Type 1, Type 2 or Type 3 responses. Type 1 responses were defined as those types of EMI responses that could or would be highly clinically significant including life-threatening responses. Other types of responses, which could simply be annoying, were categorized as Type 2, and others, Type 3, are really of no relevant clinical significance. An example of a Type 3 response would be when a pacemaker detects that EMI is present and goes into a fixed rate safety pacing mode (also known as noise reversion). This is not particularly desirable, but it is also not harmful to the patient for short periods of time. However, a Type 1 response would include, for example, prolonged pacemaker inhibition. This would mean that the pacemaker stopped delivering its life-giving output pulses. This could very quickly be life-threatening for a pacemaker-dependent patient.

Almost all modern pacemakers and ICDs incorporate feedthrough capacitor EMI filters to protect them against high frequency emitters, such as cellular telephones, microwave ovens and the like. U.S. Pat. Nos. 5,333,095; 4,424,551; and 6,765,779 illustrate and describe examples of such prior art feedthrough capacitor EMI filters.

FIG. 2 illustrates a prior art unipolar hermetic terminal 20 typically used in active implantable medical devices. Hermetic terminals typically consist of an alumina insulator 22 which is gold brazed 24 to a ferrule 26. In turn, the ferrule is typically laser welded 28 to the titanium housing 30 of an active implantable medical device. There is also a hermetic seal 32 that is formed between the alumina insulator 22 and the lead 34. This is typically also done by gold brazing, glass sealing or the like. There is also a prior art ceramic feedthrough capacitor 36 shown co-bonded to the hermetic terminal subassembly. Such feedthrough capacitors 36 are well known in the art for decoupling and shielding against undesirable electromagnetic interference (EMI) signals, such as those produced by cellular telephones, microwave ovens and the like. See, for example, U.S. Pat. Nos. 4,424,551; 5,333,095; 5,905,627; 6,275,369; 6,566,978 and 6,765,779.

FIG. 3 is a partial cutaway view showing the details of the prior art feedthrough capacitor 36 of FIG. 2. One can see that it has internally embedded electrode plate sets 38 and 40. Electrode plate set 40 is known as the ground electrode plate set and is coupled to the capacitor's outside diameter metallization 42. The active electrode plate set 38 is electrically connected to the capacitor inside diameter metallization 44.

FIG. 4 is a schematic diagram of the prior art feedthrough capacitor 36 illustrated in FIGS. 2 and 3. Prior art feedthrough capacitor EMI filters are generally of relatively low capacitance value (generally below 10,000 picofarads). As shown in schematic of FIG. 4, it forms what is known in the art as a single element low pass filter.

Due to size and other limitations, the capacitance value of these prior art low pass feedthrough capacitors is relatively low in value. Because of its low capacitance value, the filter is not effective at attenuating low frequencies, such as for LF readers. In fact, in the LF reader frequency band of 125 to 135 kHz, prior art feedthrough capacitor filters provide less than 0.5 dB of attenuation. These prior art filters are particularly effective, however, for UHF readers operating at 915 MHz. In these bands, the AIMD filter provides well over 30 dB of attenuation and in many cases, above 50 dB.

The results from the FDA studies of pacemakers and ICDs with RFID readers exactly correlate with this. There were no Type 1 responses for any UHF reader operating at 915 MHz. However, for LF and HF readers, the FDA documented a high number of life-threatening Type 1 responses out to a distance of 60 cm.

FIG. 5 is a family of curves which illustrates the performance of the prior art feedthrough capacitors illustrated in FIGS. 2, 3 and 4. In FIG. 5, one can see that the attenuation in decibels (dB) varies with frequency. These are also known in the art as single element low pass filters. In prior art pacemakers and implantable defibrillators, the inventors have found that the value of the feedthrough capacitor, which is intended to provide protection to EMI from cellular telephones, generally varies from 400 picofarads up to about 4400 picofarads (a very few designs go as high as 10,000 picofarads). One can see in FIG. 5 that at 915 MHz, all of the feedthrough capacitor values offer substantial attenuation (above 30 dB). This is why in the FDA studies, no clinically significant Type 1 EMI responses to pacemakers and ICDs at the 915 MHz RFID frequency were found. However, when one examines the 13.56 MHz frequency, one will see that high value feedthrough capacitors (in the range of 2700 to 4400 picofarads) offer a substantial amount of attenuation which varies from 17 dB to approximately 23 dB. However, some pacemaker/ICD manufacturers use relatively low value feedthrough filters in the 400 to 1200 picofarad range. In general, those do not offer sufficient attenuation at 13.56 MHz. This is why some manufacturers of pacemakers and ICDs exhibited no problems during the FDA HF testing (no Type 1 responses) whereas other pacemakers did show Type 1 responses. It should also be noted that on FIG. 5, LF (125 to 135 kHz) is substantially to the left (not shown) on the frequency axis. In FIG. 5, the frequency axis starts at 1 MHz and goes up to 915 MHz. For LF, no matter what the value of the feedthrough capacitor (from 400 to 10,000 picofarads) the attenuation is less than 0.5 dB. In other words, prior art feedthrough capacitors are totally ineffective at LF RFID frequencies and there is virtually no passive filter protection at LF frequencies at all for pacemakers and ICDs.

Passive filters include capacitors, inductors and resistors. The word "passive" means that, unlike electronic active filters, passive filters do not require a power source. Passive filters are preferred for EMI low pass filters because they can handle very high amplitude signals (like EMI from cellular phones or RFID readers) without becoming non-linear. Active filters can be designed to operate at LF frequencies. However, since they are based on very low voltage micro electronic circuit chips, they have a very limited dynamic range. It has been demonstrated that active filters become very non-linear and ineffective in the presence of high amplitude signals such as those produced by cellular phones or RFID readers. Accordingly, the AIMD manufacturer really does not have any practical design options to provide effective EMI filtering at LF RFID reader frequencies. Active filters become non-linear in the presence of high intensity RFID fields which rules them out. For an implanted passive filter to be effective at LF, it would need to be several orders of magnitude higher in capacitance value compared to prior art feedthrough capacitor filters. This would make it much too large in both volume and weight (the passive filters would almost be the size of a modern pacemaker). Worse yet, such passive filtering on the therapy delivery or sense circuits of a pacemaker or ICD would degrade its essential performance (pulse degradation, ability to sense biologic signals, etc.).

FIG. 6 illustrates typical (text book) sensing curves for both pacemakers and ICDs. The approximate center of these curves, where the devices are the most sensitive, is around 10 to 100 Hz. This means that signals that fall within this passband are meant to be sensed by the pacemaker. In the case of an ICD, this would be down in amplitude as low as approximately 100 micro-volts and for a pacemaker approximately 0.8 millivolts. This is a range of biologic frequencies that are produced by the human heart. It is important that the pacemaker sense these frequencies so that it can inhibit in the presence of a proper heart beat (proper sinus rhythm). This is an important battery saving feature as there is no reason for the PG to supply voltage pulses if the patient has his own "normal" sinus rhythm. This also prevents a condition called rate competition, which is a situation where if the pacemaker did not inhibit and the pacemaker patient had his own return to sinus rhythm, the pacemaker would actually compete with the patient's underlying rhythm.

It is instructive to look at FIG. 6 and reflect on what happened a number of years ago when there were numerous reports of cellular telephones interfering with cardiac pacemakers and ICDs. Obviously a cellular telephone transmits at much higher frequency than that as illustrated in the sensing curves shown in FIG. 6. However, what happens is that a high frequency carrier, such as that of a cellular telephone which is around 1000 MHz, would enter into previously unfiltered pacemakers and encounter a nonlinear circuit element such as a protection diode. These nonlinear circuit elements act as a demodulator. One of the worst offenders was the old TDMA 11 Hz modulated cellular telephone. Even though it operated at very high frequency, the nonlinear diode elements of a pacemaker would demodulate or strip off the 11 Hz modulation signal, which would fit right into the sensitive portion of the pacemaker passband of FIG. 6 and be oversensed. Oversensing means that the pacemaker would incorrectly interpret this 11 Hz EMI modulation as a normal cardiac heartbeat and inhibit. This is particularly life-threatening for a pacemaker dependent patient whose every heart beat depends on a proper pulse from the pacemaker. Having the pacemaker stop working or inhibit in this situation is immediately life-threatening.

With this understanding, one can now look at the table of FIG. 7. It is extremely unfortunate that the RFID industry has chosen modulation frequencies that fall generally in the range that would fit into the most sensitive portions of both the ICD and pacemaker passband sensing curves. For example, referring to FIG. 7, one sees listed here thirteen different types of RFID readers that were recently tested by the FDA shown in the left hand column. For example, RFID Equipment Code 2 operates at 134 kHz (0.134 MHz), but has a modulation of 14.43 Hz. It was predicted by the members of the Association for the Advancement of Medical Instrumentation Pacemaker Electromagnetic Interference Task Force PC69, that this was likely to be a problem. In fact, in the FDA laboratory tests, all of the LF and many of the HF RFID readers that had pulse repetition rates within the pacemaker passbands indeed caused pacemaker inhibition and/or other types of highly clinical significant Type 1 life-threatening responses. It is also interesting to note, referring to FIG. 7, that the readers that are marked CW (continuous wave) have no modulation content. These CW readers exhibited no Type 1, 2 or 3 responses to pacemakers or ICDs. One might be tempted to immediately jump to the conclusion that a simple way around this entire problem would be to simply restrict the RFID industry to only use CW readers. The problem with that is that CW readers, by definition, can only activate a tag and detect the presence of a tag and can obtain only very limited information. In other words, they can't really transmit back and forth (read/write) any detailed useful information. Accordingly, use of CW tags and readers will not allow for full identification of model number, serial number, and patient information related to an AIMD.

The FDA has conducted two extensive trials testing both pacemakers and ICDs in a laboratory environment wherein cardiac pacemakers and implantable cardioverter defibrillators (ICDs) and their associated leads were placed into human phantom saline tanks and exposed to various model RFID readers and associated systems. FIG. 8 summarizes the testing that was performed by the FDA-CDRH in 2006 and 2008. There were a total of 37 pacemakers and 34 ICDs tested. A total of 20 RFID systems were also evaluated. This testing was blinded in that the results were given letter codes so that no one reading the reports could tell who was the manufacturer of the particular pacemaker or who was the manufacturer of the particular RFID system. Referring once again to FIG. 8, it should be noted that all the major pacemaker and ICD manufacturers in the world participated in this testing by providing their devices.

FIG. 9 is a top down view of a grid placed over the saline tank used for this testing at the FDA. In 2006, a spiral lead configuration was used in accordance with ANSI/AAMI Standard PC69. In 2008, a more representational human implant geometry was used based on the distances of the lead bodies and electrodes from the pulse generator observed on patient X-rays.

FIG. 10 shows a similar set up for ICDs. On the right hand figure (2008), one can see a loop L representative of where excess leadwire would be wound up either in or adjacent to a left pectoral ICD pocket. The configuration is typical for leads passing from the left pectoral region to terminate in the right ventricle and right atrium.

FIG. 11 is a cross-section of the human phantom saline tank showing the implant (pacemaker or ICD) just below (0.5 cm) the surface of the fluid. It has been shown in the past that this type of model very accurately represents the fields that will occur inside the human body. Saline solution of 500 ohm-cm is used in the tank, which replicates the dielectric properties of body fluids. Thus, such a saline tank closely replicates the EMI characteristics encountered by a device that has been implanted inside the human body. The testing, as performed by the FDA, was done with the antenna suspended in a robotic arm that could carefully step the RFID antenna away in discrete distances so that accurate threshold distances for Type 1, 2 and 3 responses could be recorded.

The following definitions are provided to assist with a better understanding of the ratings applied to the FDA electrocardiogram (EKG) tracings in FIGS. 12 through 20. Class 1 responses include transient ventricular inhibition for 3 seconds or more, persistent ventricular inhibition or any change in pulse generator programmed settings. It should be noted that throughout all of the RFID testing, to be discussed in more detail below, there was never a change in programmed settings. In other words, when the RFID reader was removed or turned off, the EMI response immediately ceased. Class 2 response is defined as transient (intermittent) ventricular inhibition for more than 2 seconds, but less than 3 seconds. A Class 2 response also included transient, continuous atrial inhibition or rate adaptive pacing. Class 2 responses are not considered to be immediately life threatening, but are considered to be very undesirable. For example, persistent very high rate stimulation of the heart can produce irreversible damage and/or death, particularly in heart failure patients, patients with ischemic heart disease and others. Class 3 is defined as any other type of interference which includes transient inhibition of less than 2 seconds, and/or noise reversion mode pacing. This is a software circuit feature where the pacemaker detects EMI and reverts to a non-responsive fixed rate (metronome like) stimulation. This is similar to what occurs after a magnet is applied over a pacemaker to close a reed switch, for example, to bypass the circuit that ordinarily decides whether pacing is required or not based on the feedback electrical signals that are being received from the heart. Class 3 responses are undesirable but not considered to be clinically significant.

FIG. 12 shows an EKG base line strip of a pacemaker in the saline tank without an RFID reader present. Normal pacing pulses are shown with the atrial pulses A shown on top and the ventricular pulses V shown on the bottom. One can see that every time there is an atrial pulse, a ventricular pulse follows after the programmed delay (PD). This A-V delay is a normal function as also occurs naturally during sinus rhythm within the human body. Also notice that the atrial pulses are all equally spaced as are the ventricular pulses. This is what would be observed when a pacemaker is functioning normally.

FIG. 13 is the same EKG strip as FIG. 12 except in this case an RFID reader has been brought close to the pacemaker and/or its leads in the saline test tank. High frequency (HF) electrical activity is present on the baseline. Although not in any way similar to a physiological signal, in this case, the pacemaker has incorrectly over-sensed and interpreted the RFID signal as a normal heart rhythm and has completely shut off (inhibited) pacing output (atrial and ventricular inhibition). If the patient in whom the pacing device had been implanted had no intrinsic heart electrical rhythm all of the time (was totally pacemaker dependent), or just some of the time (was partially or intermittently pacemaker dependent), the inhibition shown in FIG. 13 either would or could be immediately life-threatening, respectively. Very early on in one of the inventor's experience as a physician with demand pacemakers, this resulted in the death of a very intermittently dependent patient farmer when he was driving his tractor just as he had done many times previously without difficulty. Several identical model demand pacemakers from the same company were then tested while in the shirt pocket of someone sitting in the driver seat of the same model tractor. Inhibition was 100% in all cases caused by EMI from the tractor motor ignition system. It is important to emphasize that intermittent pacemaker dependency (and potentially dependency on other life supporting devices) is common and by its very nature, is under-reported based on the parallel intermittency of follow-up clinic visits. Even if the patient usually has an intrinsic rhythm, dependency for just a few minutes during an overlapping period of exposure to EMI will be fatal. Similarly, patients' lives and well being are frequently at risk because of lack of availability of accurate medical device and clinical data.

FIG. 14 is a pacemaker EKG strip which illustrates another type of Class 1 response involving continual or prolonged ventricular inhibition with individual episodes lasting longer than 3 seconds. As one can see, there is a ventricular stimulus (V1) at approximately 135.5 seconds and then another ventricular stimulus (V2) at 142.2 seconds. Atrial stimulus pulses are shown as A1 through A7 and are undesirably irregular (however, transient atrial inhibition is not considered life threatening). Any transient ventricular inhibition that lasts 3 seconds or more is considered a Class 1 or potentially life threatening response.

FIG. 15 is an EKG tracing which shows high frequency RFID EMI (HF EMI) on the base line tracing, which an ICD has incorrectly interpreted as ventricular fibrillation and delivered a high voltage shock (HV) after 53.4 seconds (if programmed on pacing was totally inhibited). This is defined as a Class 1 response because undesirable high voltage shocks are not only very painful for the patient, but can also result in serious accidents (an inappropriate ICD shock can knock a patient right off his feet).

FIG. 16 is a pacemaker EKG strip example of a Hayes et. al. Class 2 inhibition showing occasional atrial and ventricular output suppression. This is a Class 2 response because of lack of complete atrial inhibition and because the ventricular pulse inhibition is always at least two seconds, but for less than three seconds in duration. It should be noted that no Class 2 responses were found in any of the FDA testing (all responses recorded in the 2008 FDA study were either Class 1 or Class 3).

FIG. 17 is a pacemaker EKG strip of a typical Class 3 response. Through most of this EKG strip, one can see normal atrial (A) and ventricular (V) stimuli. However, at the 49 second point, there is an approximately 33% lengthening of the A-A (A1-A2) interval similar to what is seen with occasional T-wave over-sensing at the atrial electrode. This is of no clinical significance and many patients are unaware of a transient slowing of the stimulation rate.

FIG. 18 is a pacemaker EKG strip example of occasional atrial output stimulus inhibition (A) associated with what is most likely atrial triggered ventricular pacing (V). This would be expected with selective detection of EMI on the more sensitive atrial channel versus the less sensitive ventricular sensing circuitry. Atrial sensitivities are almost always adjusted to a low millivolt setting versus the ventricular sensitivities as the electrical signal associated with ventricular contraction is generally 4 times or greater the discharge associated with contraction of the relatively thin atrial wall muscle. Regardless, intermittent loss of atrial ventricular synchrony would rarely be life-threatening for the patient even if it persisted for a long period of time.

FIG. 19 is an EKG strip example of the injection of a CENELEC wave signal, intended to stimulate a normal biologic cardiac electrical signal, into the saline test tank. In engineering terms, the CENELEC signal is intended to represent normal heart electrical activity although the 11 Hz (660 PPM) frequency seen on the base line is more representative of poorly organized atrial or ventricular fibrillation. It is expected that a normally operating pacemaker will be completely inhibited. In other words, what FIG. 19 should look like is the EMI tracing in FIG. 13. The object of complete pacing output inhibition during normal heart rhythms is to avoid delivery of even occasional unnecessary ventricular stimuli (V), as these could result in competition between paced and intrinsic heart action in a patient. This type of interaction is also considered of minor Class 3 clinical significance.

FIG. 20 is an EKG strip example of a pacemaker apparently not responding properly to the CENELEC injection signal, the presence of which is clearly documented on the base line. The expectation was that the delivery of stimuli by the pacemaker would be completely inhibited as shown in FIG. 13, but in this case as a normal response to a satisfactory patient-generated heart rhythm. Instead, when the RFID reader was brought close to the pulse generator, the sensing circuit classified the supposedly physiologic signal as EMI and automatically switched into the noise reversion (fixed rate) pacing mode, previously outlined as part of the Hayes et al. Type 3 definition. Thus the pulse generator continued to deliver A-V sequential stimuli at regular intervals similar to what was illustrated in FIG. 12, but because of the sensing circuits being by-passed, the atrial (A) and ventricular (V) stimuli in FIG. 20, would be competitive with a patient's underlying heart rhythm. By competitive, we mean the stimuli would fall randomly onto various portions of the intrinsic cardiac action. This is not particularly desirable because while infrequent, application of electrical stimuli while the cardiac tissues are repolarizing (recharging following a muscular contraction) can be arrhythmiagenic. However, this is considered a lesser risk allowing the pacing circuits to be shut off by EMI, when all patients are potentially dependent at one time or another.

FIG. 21 is a bar graph summarizing the FDA 2006 and 2008 pacemaker test data at LF, HF and UHF RFID frequencies. Unfortunately, in 2006, pulse generator responses to the testing were not identified as clinical Type 1, 2, or 3. In other words, trivial and potentially life-threatening responses were lumped together. For example, for 134 KHz (LF) in 2006, 83% of pacemakers tested showed an EMI response. However, the 2008 test stratified the LF data to reveal that 46% of the pacemakers had a Type 1 (life-threatening) response, whereas 32% had a Type 3 response and 22% of the devices were entirely unaffected (these were all unmodulated CW readers). Note: there were no Type 2 responses. A similar range of responses and effects were noted during the testing of the 13.56 MHz (HF) readers. In 2006, a total of 18% of units were affected by the EMI, whereas in 2008, this was refined to show that 7% of devices had a Type 1 response and 4% had a Type 3 response. In 2006, at UHF frequencies, 6% had a response, but this represents only a single pulse generator. It was later determined that this particular pacemaker model did not have a feedthrough capacitor filter. This situation was since rectified through manufacturer re-design. Accordingly, in 2008, none of the pulse generators were affected by any of the readers transmitting 915 MHz signals.

FIG. 22 is a bar graph summarizing the FDA test data that is very similar to FIG. 21 except it's for ICDs. It should be noted that 55% of ICDs tested in 2008 at LF showed a Class 1 reaction. This is unfortunate because 134 kHz is an ideal frequency for continuous reader signal emissions to decode a tag embedded deeply inside of body tissue, within the header block, or even inside the housing of an active implantable medical device.

FIG. 23 is a comparison of all of the different types of LF readers tested by the FDA. The reader numbers 1, 2, 3, 4 and 5 correlate with the same RFID equipment code numbers previously described in FIG. 7. As one can see, for RFID reader #1, which was CW, there was no deleterious effect on any of the pacemakers tested. Reader #3, which has a modulation of 11 Hz, effected the greatest number of pulse generators (61% Class 1 and 31% Class 3). This is not particularly surprising if one refers to FIG. 6 and sees that the most sensitive part of both the pacemaker and ICD sensing curves occur at about 11 Hz. The main take-away or summary from FIG. 23 is that all of the modulated low frequency (LF) readers have the potential to cause dangerous pulse generator responses (Class 1) in essentially every case. As previously explained, pacemakers and ICDs really have no practical defense (EMI Filter) to an LF signal that contains modulation within their passband.

FIG. 24 is a bar graph very similar to FIG. 23 except that it compares LF reader FDA test results for ICDs. Again, use of CW reader #1 had no ill effects. However, with reader #3, which has a modulation of 10.5 Hz (which falls right into the ICD sensing passband of FIG. 6), 81% of all responses were Type 1, that is, associated with high clinical risk.

FIG. 25 is a bar graph which is very similar to FIGS. 23 and 24. However, this is a comparison of pacemaker responses at the 13.56 MHz (HF) RFID carrier frequency. Again, reader #8, which is CW, had no effect on any of the pulse generators tested. However, readers #6 and #10 both with 11 Hz modulation resulted in the most detrimental pulse generator responses (13% Type 1 in both cases).

FIG. 26 is a bar graph which illustrates FDA tests using the same HF readers and carrier frequencies as FIG. 25, but for ICDs. Under these test conditions, ICDs tend to be much less susceptible to adverse reader effects than pacemakers. This is likely due to the fact that ICDs are slower to react in providing a high voltage shock as it takes time to charge their high energy internal capacitor, and before pulse delivery a re-interrogation takes place to make sure the dangerous tachyarrhymia is still present.

FIG. 27 summarizes the threshold distances for EMI reactions in the FDA RFID reader testing. The greatest distance at which any reaction was documented was out to 60 cm. This is of great concern compared to the original cell phone work where it was determined that maintaining a transmitter to pulse generator separation greater than 15 cm would be safe. For Type 1 life-threatening reactions, the greatest distances that could lead to an adverse effect was 40 cm with LF readers, and 20 cm for HF readers. For ICDs, the reactions tended to require closer proximity. For any reaction, the threshold distance was 40 cm. For a Type 1 reaction, the RFID reader had to be held within 12.5 cm of the implant in the saline tank. In no case were there any Type 1 reactions for UHF readers. All of these recorded threshold distances are of particular concern for an RFID reader that is designed to directly interrogate an AIMD such as a pacemaker or ICD (to determine the model number, type, serial number, etc. of the implanted device). In these cases, for example in an ambulance or emergency room, the RFID reader would be held as close as 2 cm to the implanted device. The potential for a life threatening Class 1 response is evident.

Similar concerns are present where other types of LF and HF reader applications in which a pacemaker patient or AMD/AIMD may encounter such a reader in the patient's normal environment. For example, keyless entry systems for automobiles generally operate at LF frequencies. The car itself transmits an LF RFID signal which detects the driver/passenger/patient walking up to the automobile where the automobile goes into an active (pinging) mode generating a powerful LF frequency to detect the approach of the driver or passenger who may also possibly be an AIMD patient. When the person nears the car with the car's RFID tag either in his pocket, associated with a wrist watch or other type of container (like a purse or wallet), the car door will automatically unlock (open). Some new automobiles also incorporate a back-up RFID reader system in the driver's seat. For example, in some models, an RFID antenna is also embedded within the driver's side seat back wherein the car tag is reinterrogated to make sure the correct person is inside the car before the ignition will start (this is an anti-high jacking feature). Of course, all of this is of great concern if the particular driver happens to be a pacemaker or ICD patient.

Accordingly, there is a need for an RFID interrogation/communication system having built-in safeguards for protecting sensitive device electronics against RFID-associated electromagnetic interference (EMI). More particularly, an RFID communication system is needed for protecting active medical devices against RFID-associated EMI. Such systems must be able to identify active and passive medical devices through use of RFID technology without causing the AIMD or PMD to malfunction. The present invention fulfills these needs and provides other related advantages.

SUMMARY OF THE INVENTION

The present invention generally resides in an RFID communication system for protecting a medical device or an electronic circuit against RFID-associated electromagnetic interference. The system comprises a radio frequency identification (RFID) communicator which includes a circuit for limiting the total continuous transmit time of an electromagnetic signal. The communicator also includes a time-out circuit for delaying a subsequent transmission of the electromagnetic signal. The electromagnetic signal may comprise an RFID test signal, an RFID tag search signal, an RFID communication signal, an RFID interrogation signal, an RFID read signal, or an RFID write signal. The electromagnetic signal may be modulated or unmodulated.

The total continuous transmit time of the electromagnetic signal is preferably no greater than five seconds. In a particularly preferred embodiment, the total continuous transmit time of the electromagnetic signal is five hundred milliseconds or less and the time-out circuit delays the subsequent transmission of the electromagnetic signal for two seconds or more.

The communicator may comprise a read-only or a reader/writer device. The communicator may be actively searching for or communicating with an RFID tag (even if no tag is present). The communicator may be in communication with a computer or a computer network.

The RFID tag is associated with an object in close proximity to a patient having an active medical device, or is associated with the medical device. The RFID tag may comprise a read-only or a readable/writable RFID tag. Typically, the RFID tag comprises an antenna and an electronic microchip electrically connected to the antenna. The RFID tag may include retrievable information relating to the active medical device and/or patient. The retrievable information may include information pertaining to MRI compatibility of the active medical device or an associated lead system.

The active medical device may comprise any of the following: a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, an endovascular catheter, a Bion or a prosthetic device, and component parts thereof, including lead wires and abandoned leads. The object in close proximity to the patient may comprise passive medical devices and components thereof, including any of the following: heart valves, stents, screws, plates, hip implants, knee implants, prosthetics, braces, wristbands, necklaces, identification badges or cards, ankle bracelets, or eyeglasses.

The RFID reader/writer (communicator) may include a barcode reader. The communicator may write data received by the barcode reader to an RFID tag.

The communicator may transmit an interrogation signal to the RFID tag when the communicator senses that the RFID tag is in close proximity. In such a case, the communicator will actively seek an associated RFID tag.

The communicator may comprise a portion of an animal or an article tracking system. For example, the tracking system may comprise a hospital patient monitoring system which may track the patient. Such a system may also be used as a medication tracking system. The communicator may also comprise a portion of an electronic article surveillance (EAS) system, be incorporated into a check-out station for purchase of goods, or as part of an automobile system, such as an entry and security system.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 2 is a fragmented sectional view of a prior art unipolar hermetic terminal typically used in active implantable medical devices.

FIG. 3 is an enlarged, partially fragmented perspective view of the feedthrough capacitor shown in FIG. 2.

FIG. 4 is a schematic electrical diagram of the coaxial feedthrough capacitor of FIG. 3.

FIG. 7 is a table showing all of the RFID readers that were tested in a 2008 battery of tests.

FIG. 8 is a summary of the testing that was performed by the FDA-CDRH in 2006 and 2008.

FIG. 27 is a summary of interaction distances.

DETAILED DESCRIPTION OF THE PREFERRED EMBODIMENTS

The present invention is directed to novel RFID communicators (readers/interrogators) that include a circuit for limiting the total continuous transmit time of an electromagnetic signal, and a time-out circuit for delaying a subsequent transmission of the electromagnetic signal. By limiting the total continuous transmit time of the electromagnetic signals, in the case of a cardiac pacemaker, only a few beats could be dropped, which is clinically insignificant to the patient. In other words, by limiting the transmit time and having a time-out period, the RFID communicator cannot transmit for a sufficiently long enough period to permanently harm the patient or cause a life-threatening arrhythmia.

Figure 1:
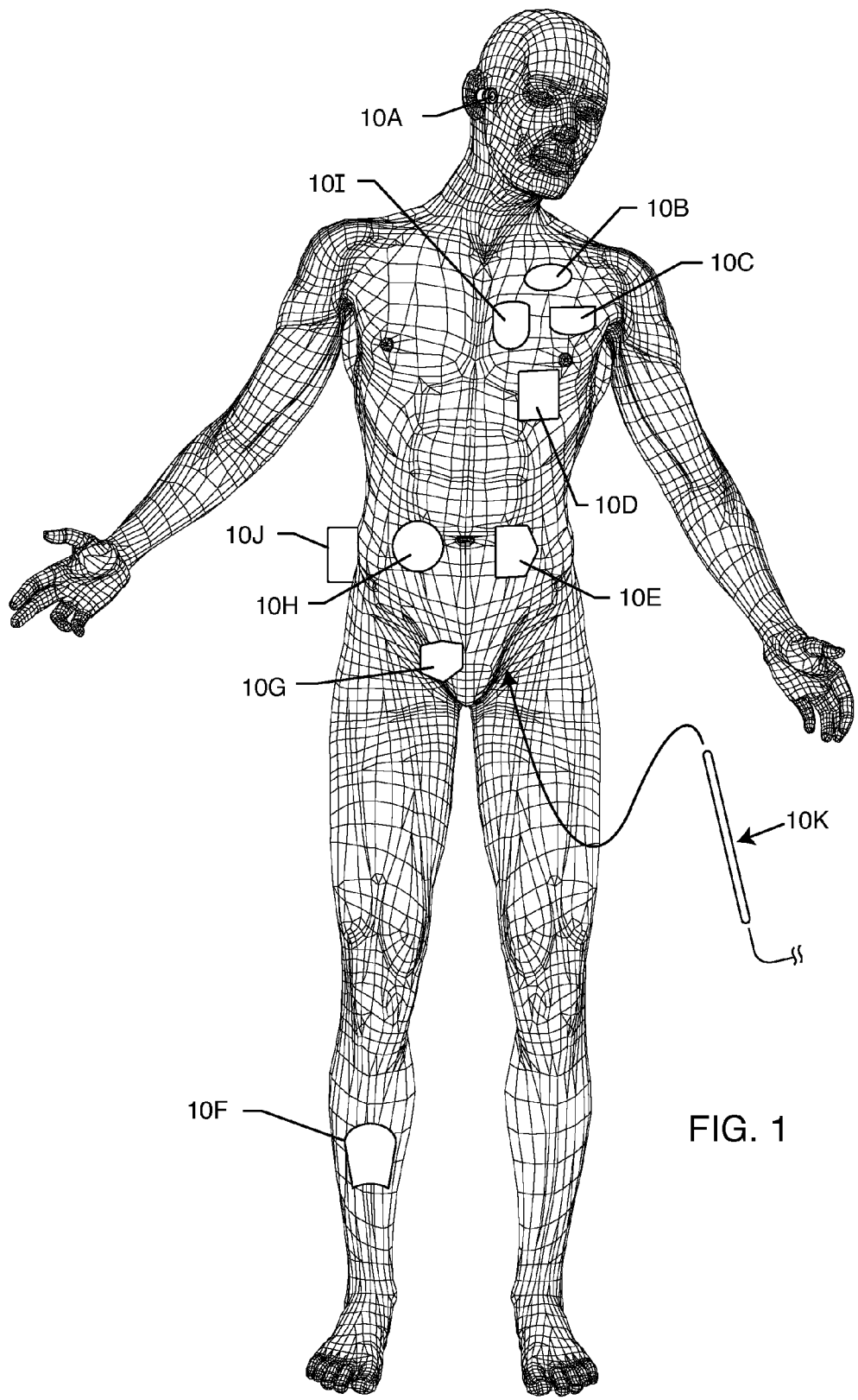
FIG. 1 is a wire-formed diagram of the generic human body showing a number of active and passive medical devices (AIMDs and PIMDs).
Figure 5:
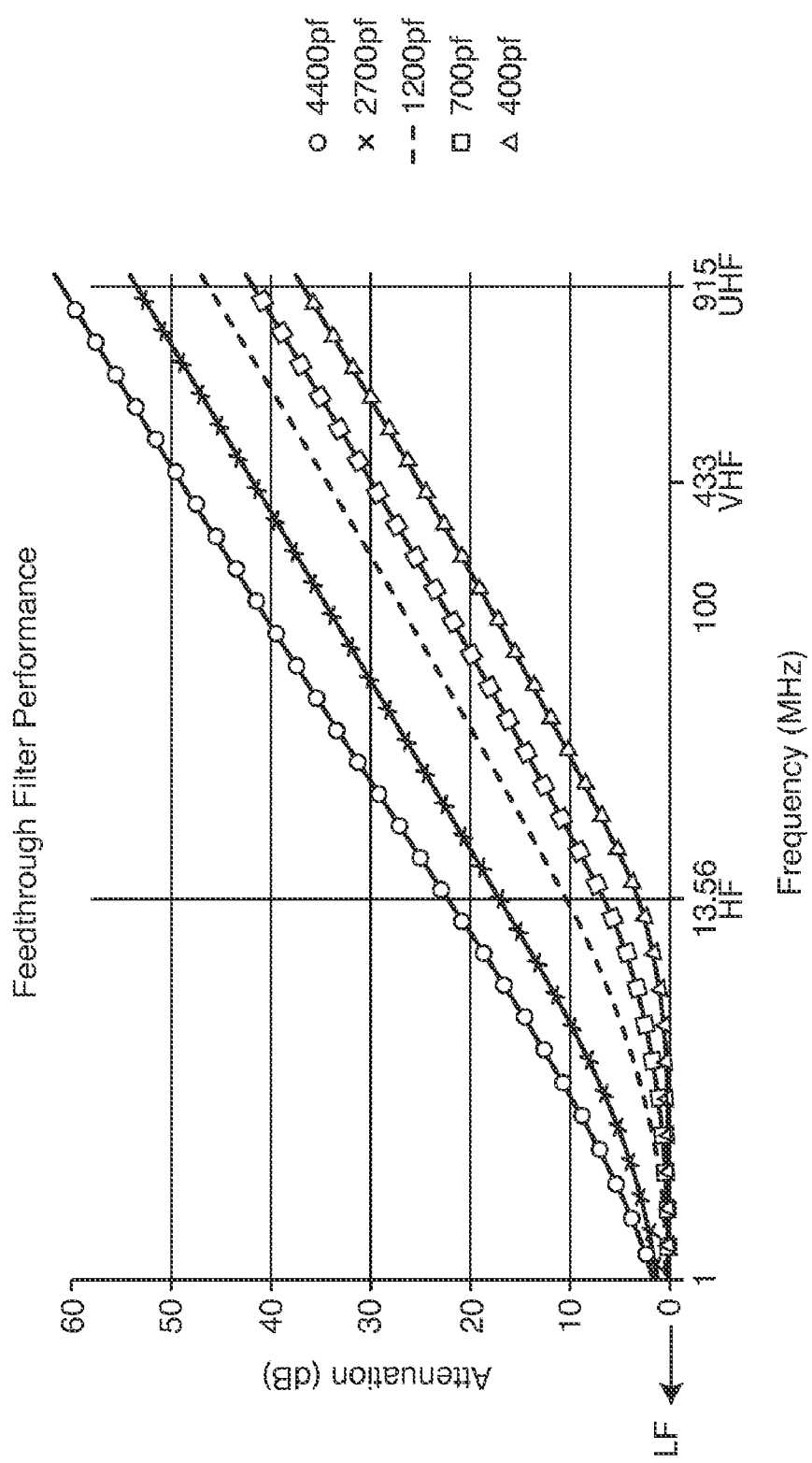
FIG. 5 is a graph illustrating the performance of four different feedthrough capacitors exposed to LF, HF, and UHF RFID signals.
Figure 6:
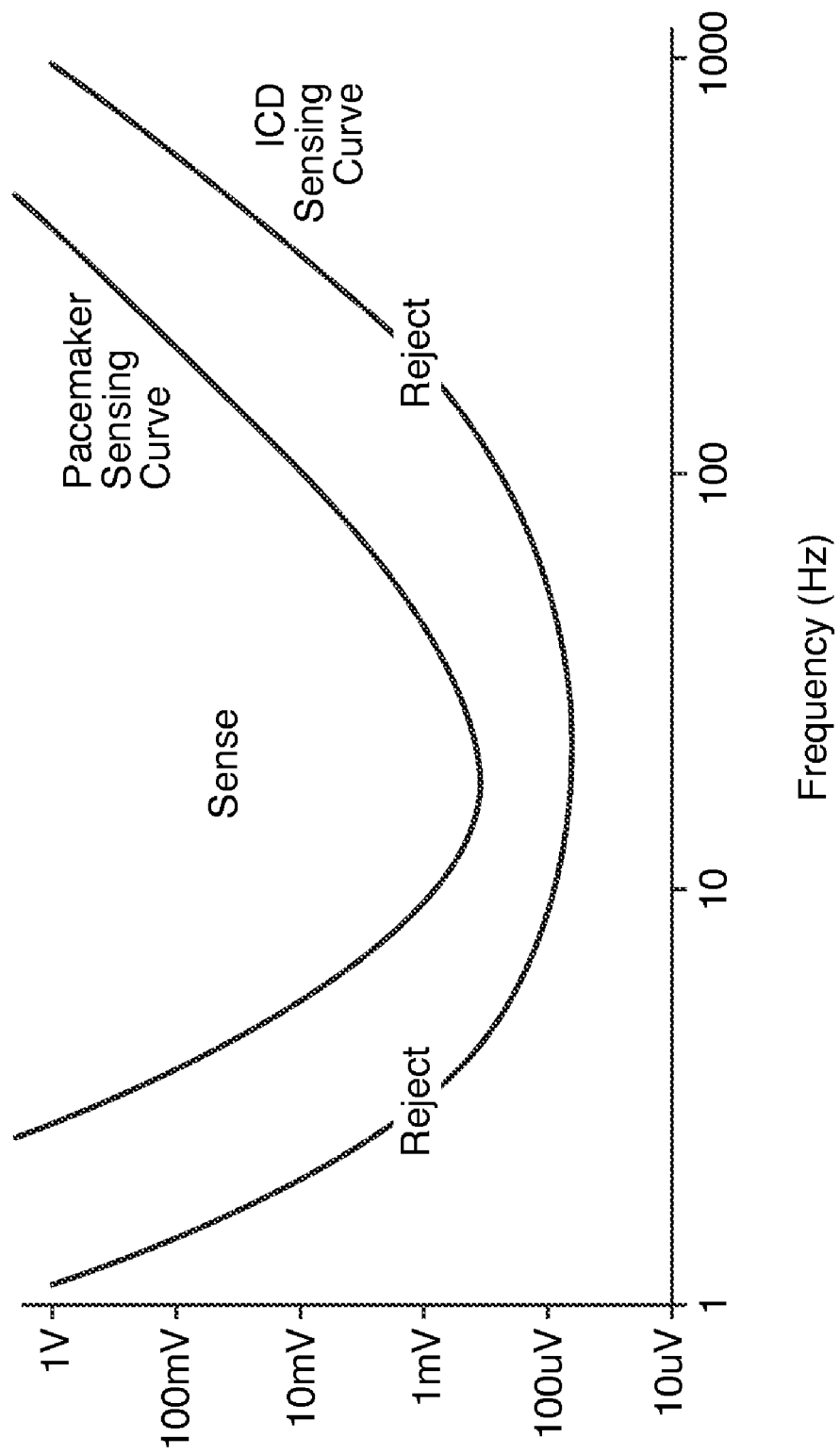
FIG. 6 illustrates a generic sensing curve for pacemakers and implantable cardioverter defibrillators.
Figure 9:
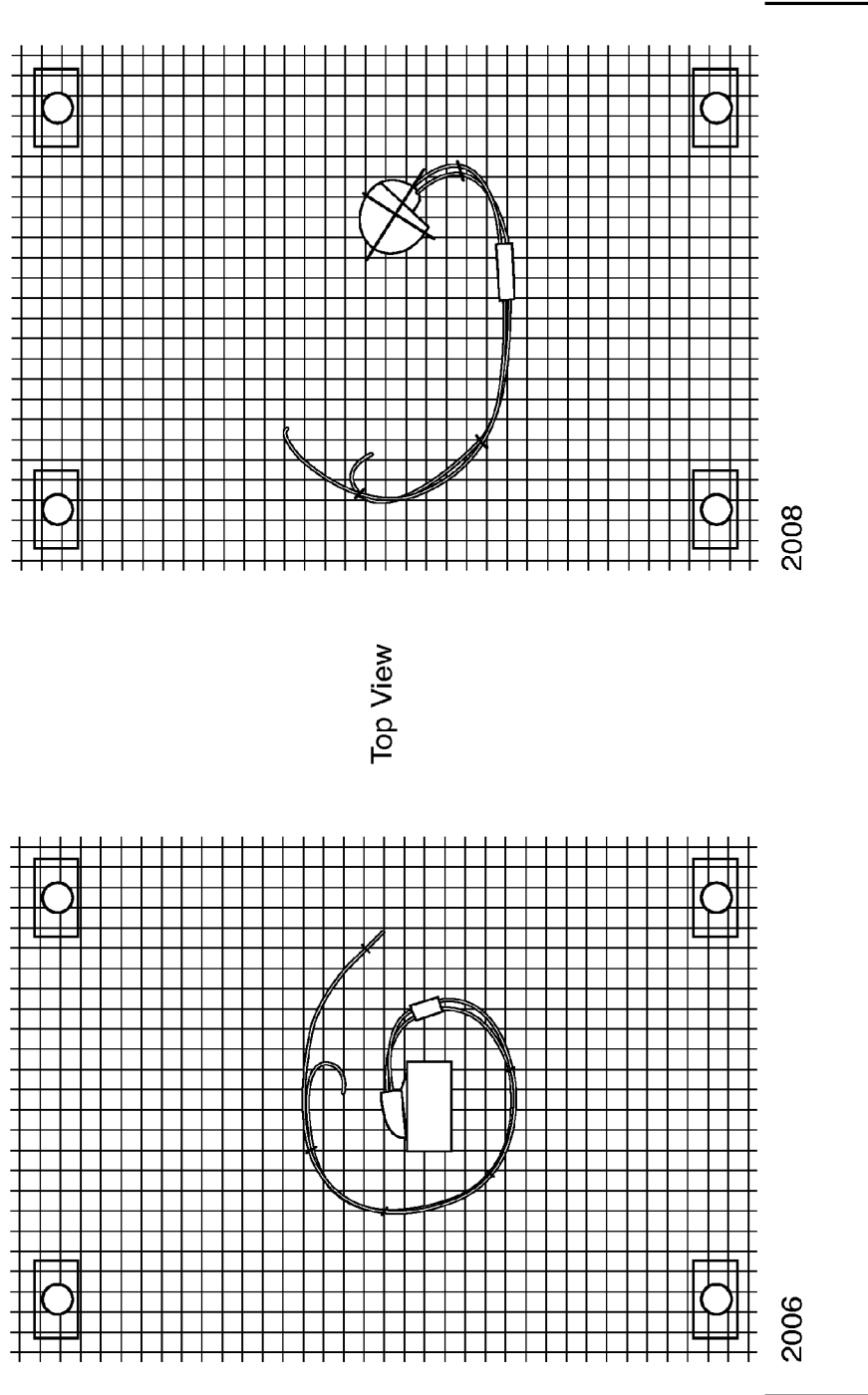
FIG. 9 is a plan view of a grid placed over the saline tank used for pacemaker testing by the FDA.
Figure 10:
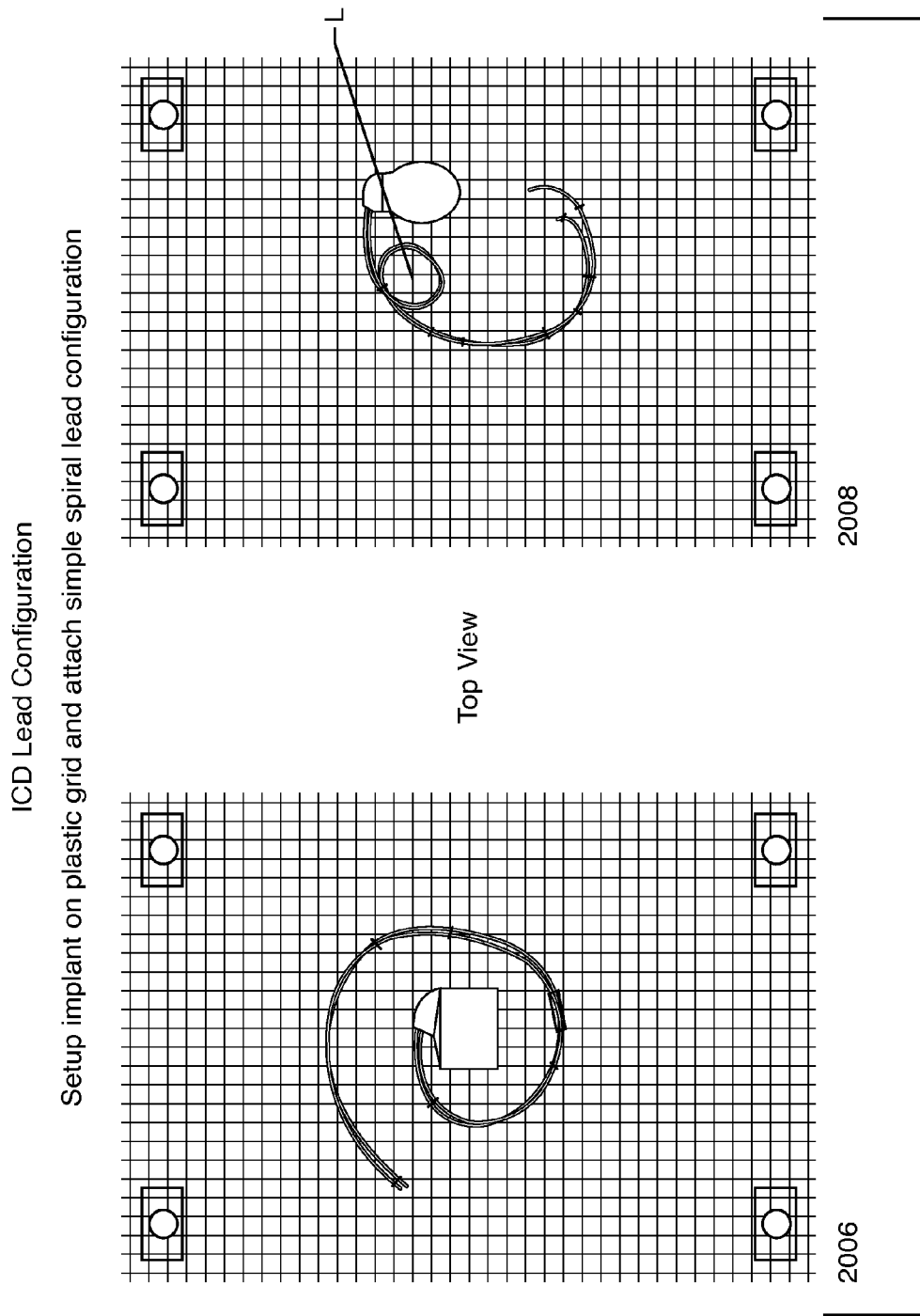
FIG. 10 is a plan view similar to FIG. 9 showing a similar setup for ICDs.
Figure 11:
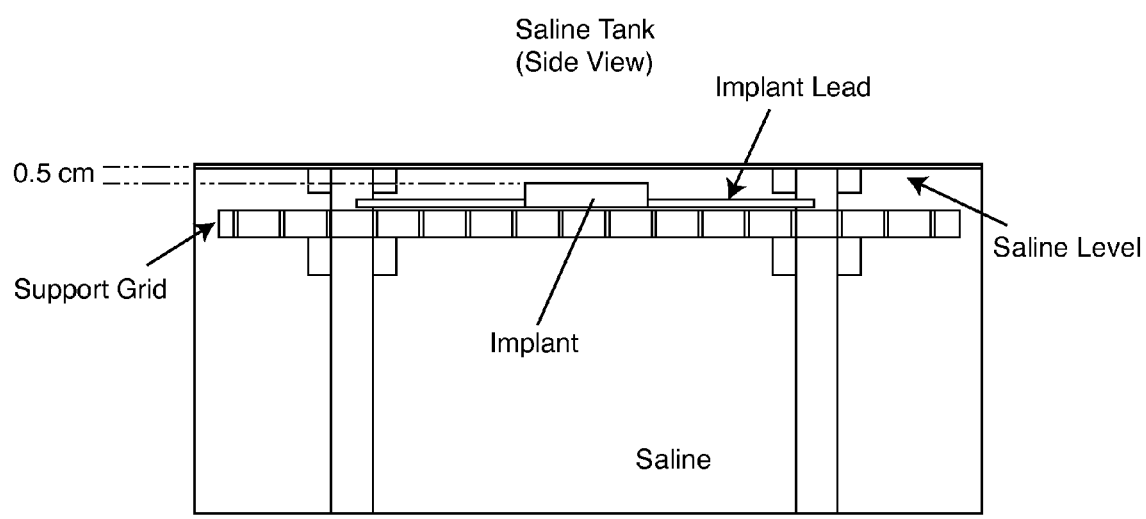
FIG. 11 is a cross-sectional view of the saline tank utilized in the testing mentioned, showing the implant just under the surface of the saline fluid.
Figure 12:
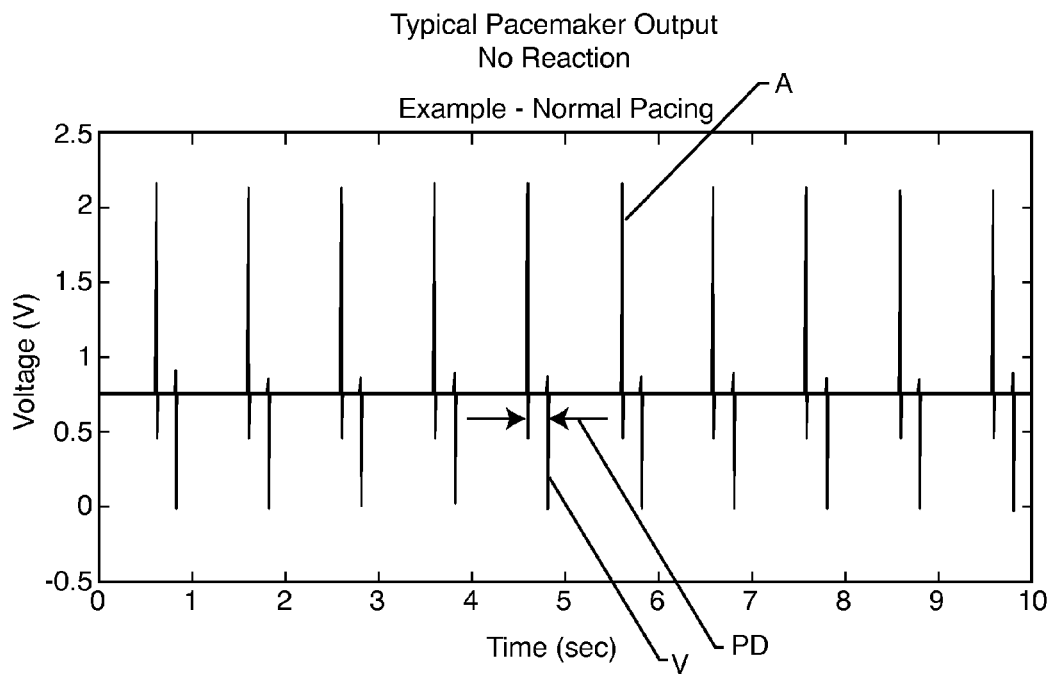
FIG. 12 shows a baseline of a pacemaker in a saline tank without an RFID reader present.
Figure 13:
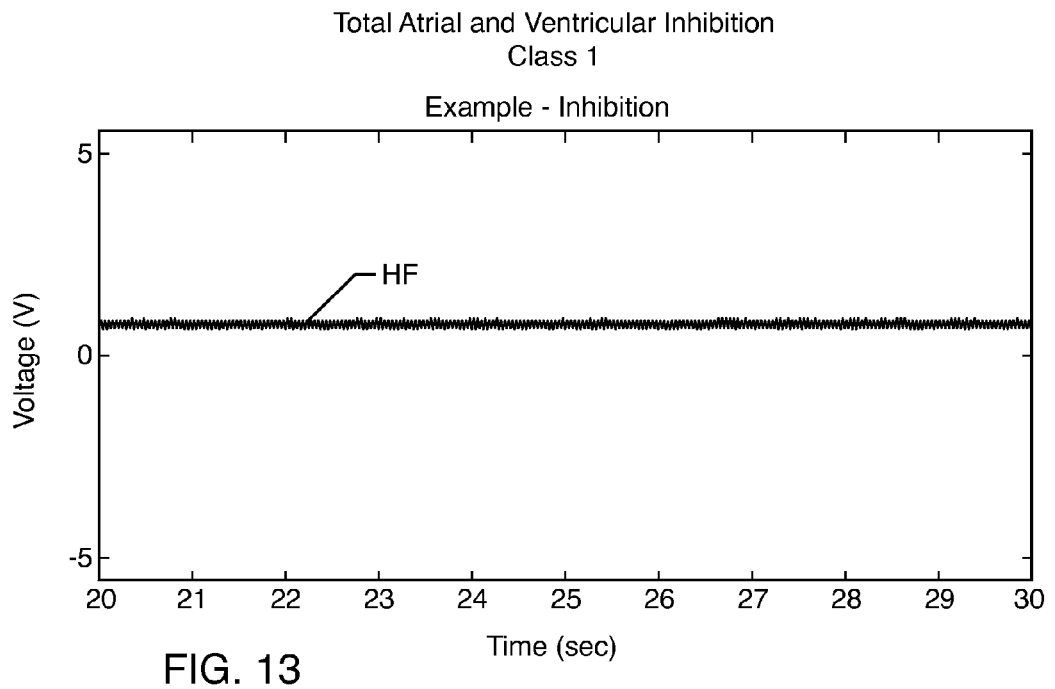
FIG. 13 is a graph similar to FIG. 12, except in this case an RFID reader has been brought close to the tank.
Figure 14:
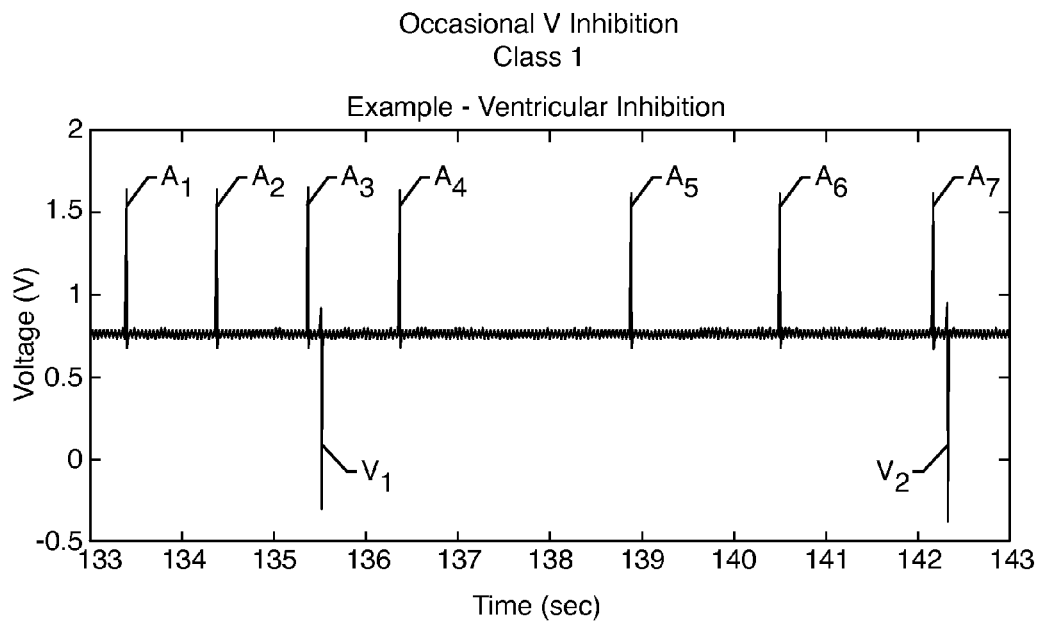
FIG. 14 illustrates a type of class 1 response involving ventricular inhibition that lasts longer than three seconds.
Figure 15:
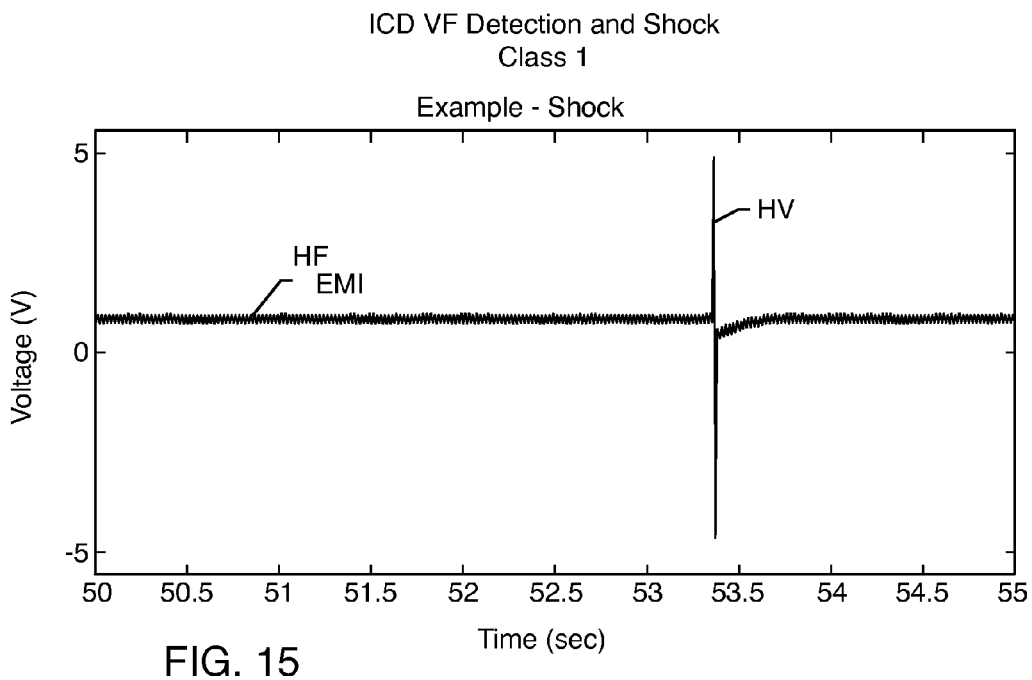
FIG. 15 illustrates the output detection on an ICD where a ventricular defibrillation was detected and a high-voltage shock was delivered if programmed pacing was totally inhibited.
Figure 16:
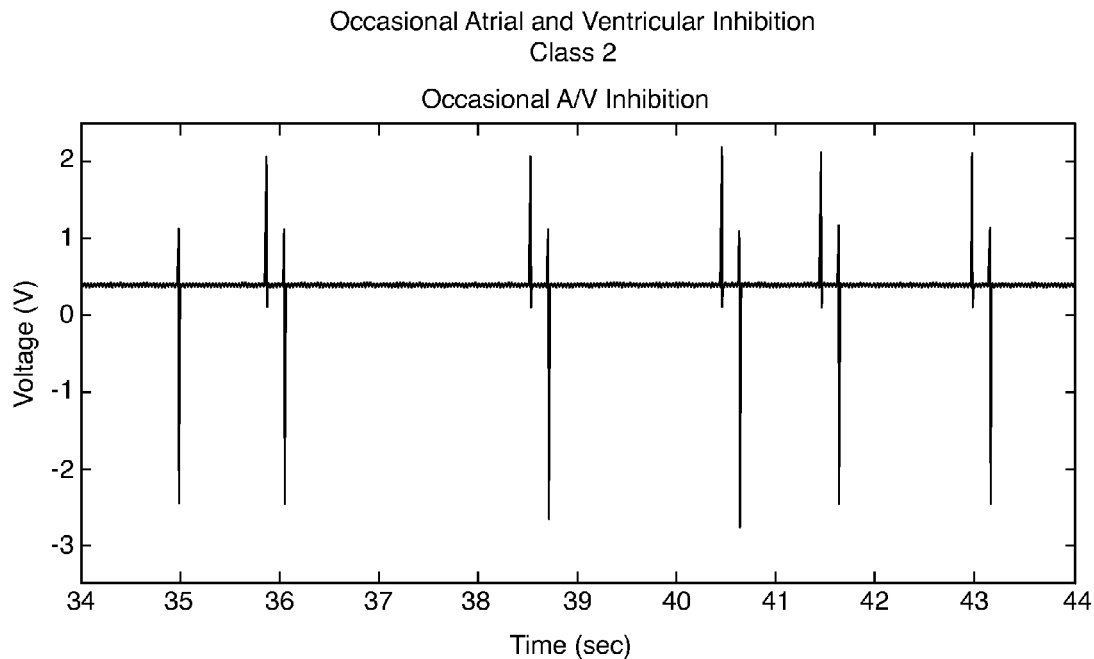
FIG. 16 is an example of a class 2 response showing occasional atrial and ventricular inhibition at a maximum duration less than 3 seconds.
Figure 17:
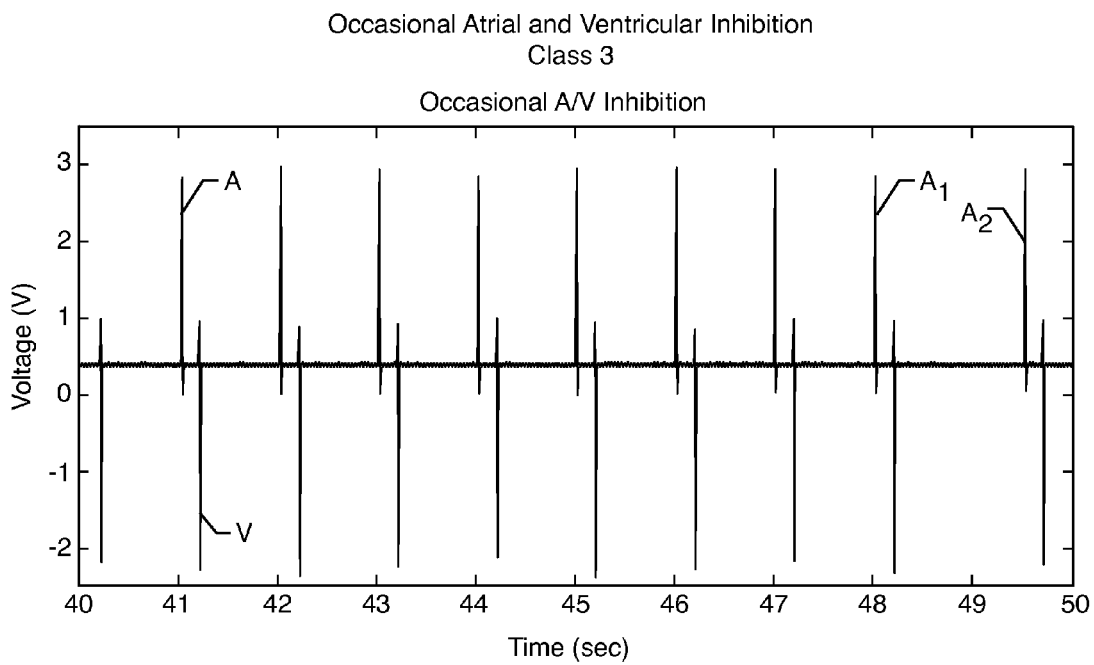
FIG. 17 illustrates a typical class 3 response—transient (less that 1 second) inhibition.
Figure 18:
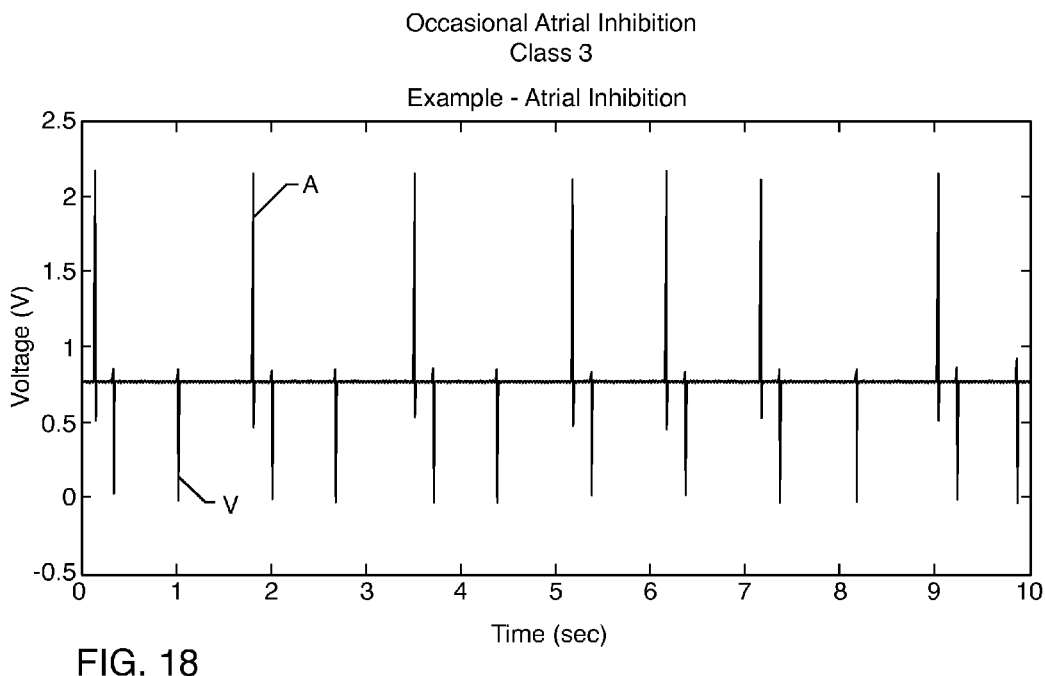
FIG. 18 is an example of an occasional ventricular inhibition and inhibition of every other atrial stimulus output.
Figure 19:
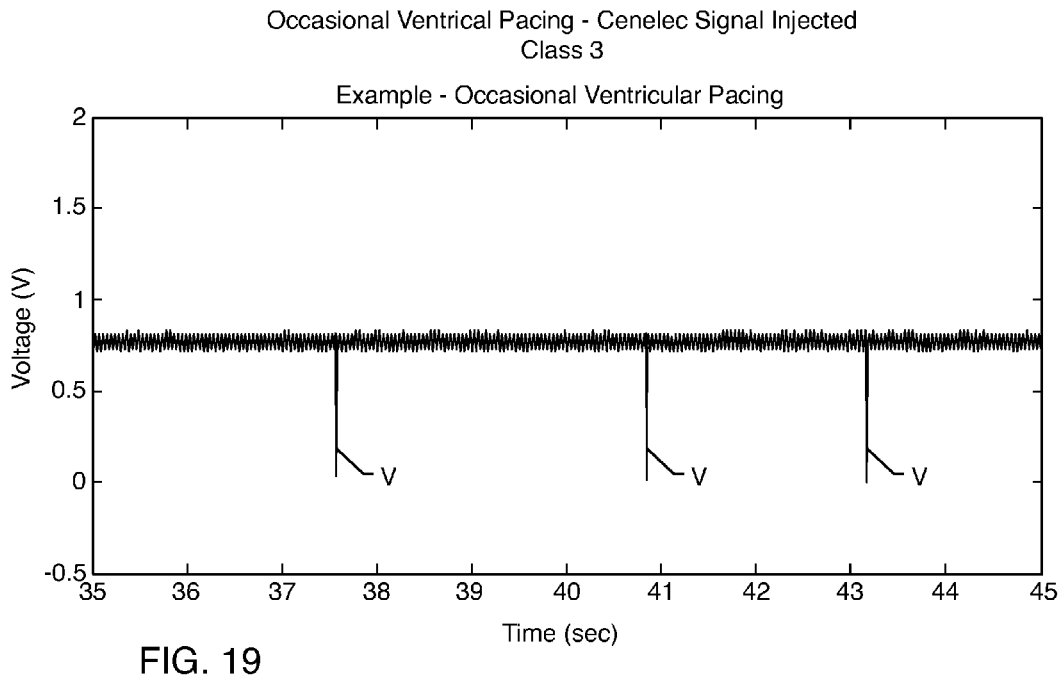
FIG. 19 shows an example of Class 3 occasional ventricular pacing.
Figure 20:
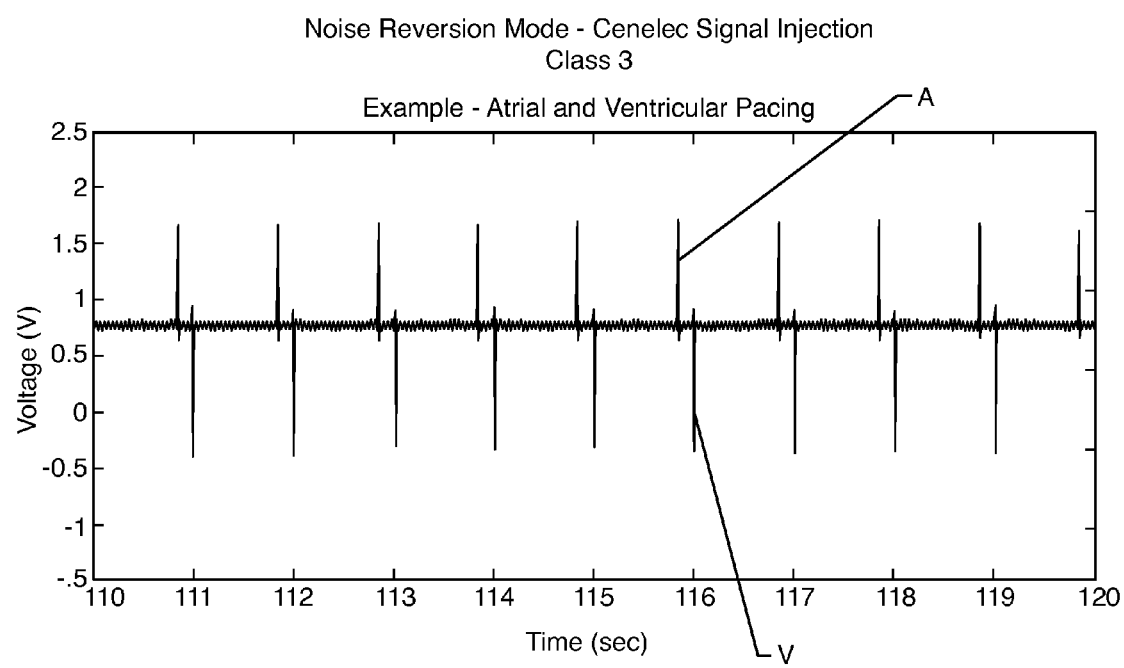
FIG. 20 is an example of a pacemaker that has responded to a CENELEC injection signal by reverting to fixed rate, potentially competitive atrial ventricular stimulus emission.
Figure 21:
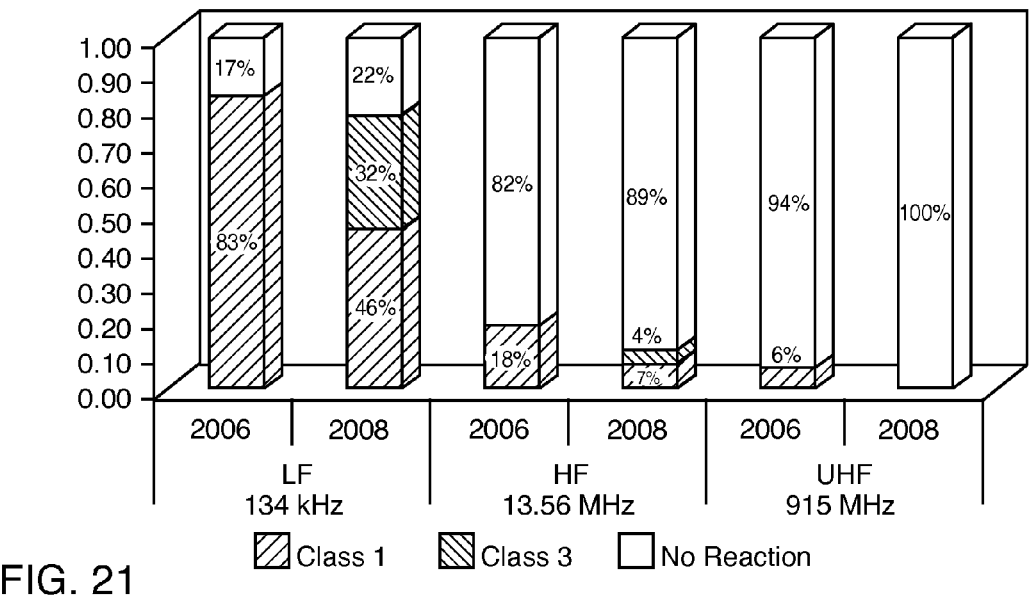
FIG. 21 is a bar graph summarizing the pacemaker data at LF, HF and UHF frequencies.
Figure 22:
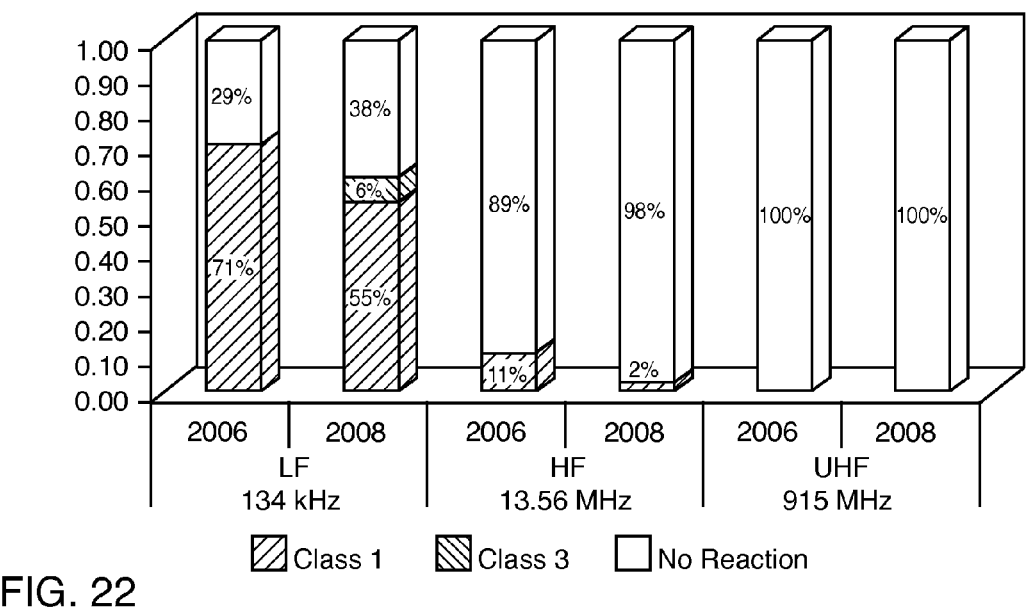
FIG. 22 is a chart similar to FIG. 21, except it is for ICDs.
Figure 23:
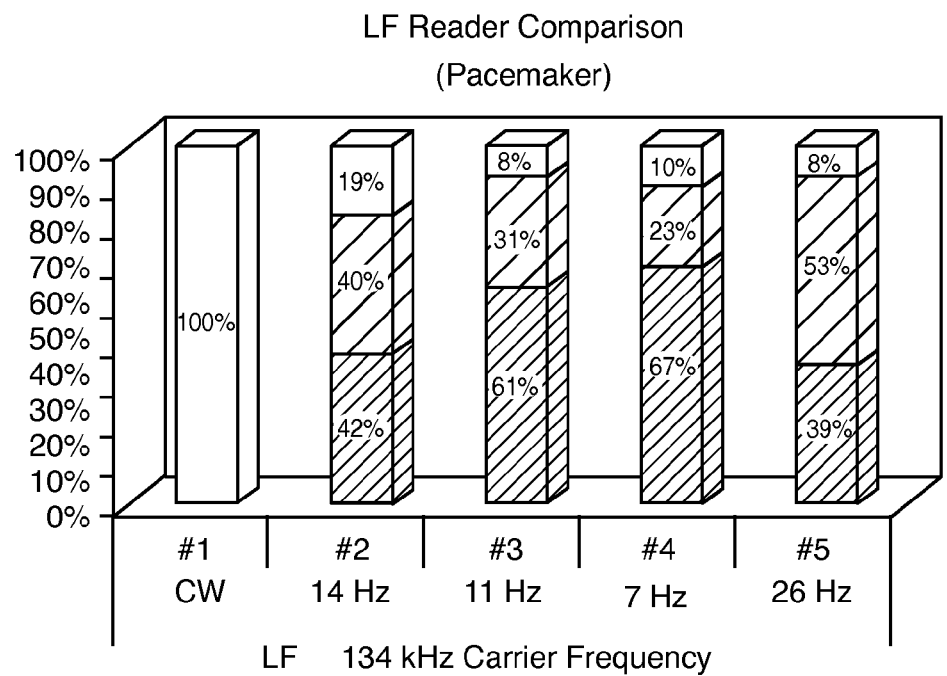
FIG. 23 is a chart showing a comparison of all the different types of LF readers for pacemakers tested.
Figure 24:
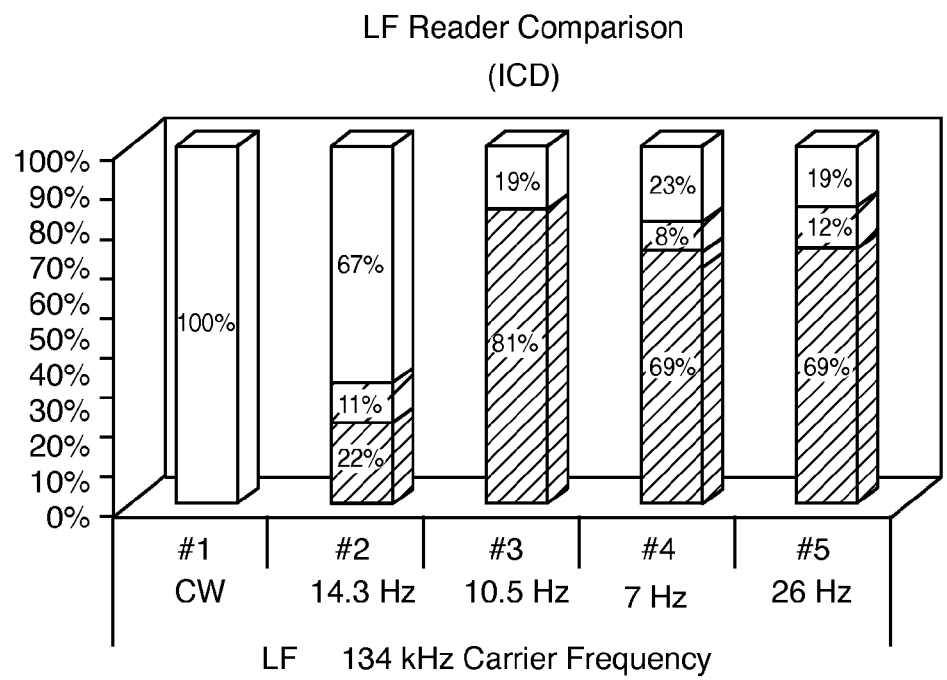
FIG. 24 is a chart similar to FIG. 23, except that it compares LF readers for ICDs.
Figure 25:
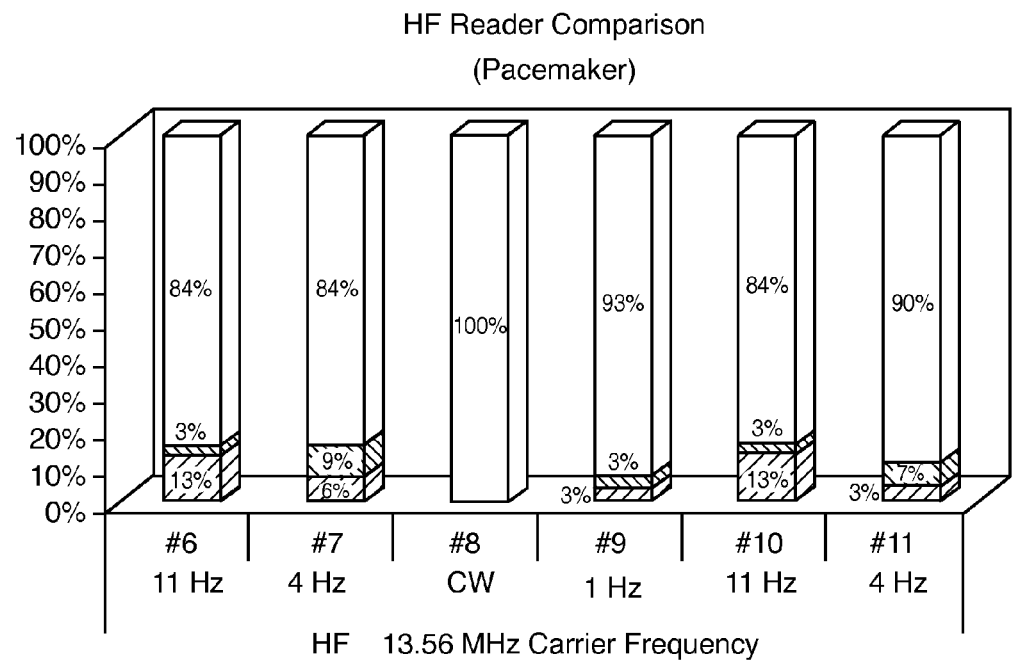
FIG. 25 is a bar graph similar to those shown in FIGS. 23 and 24, however, it is a comparison of pacemaker responses at the 13.56 MHz (HF) carrier frequency.
Figure 26:
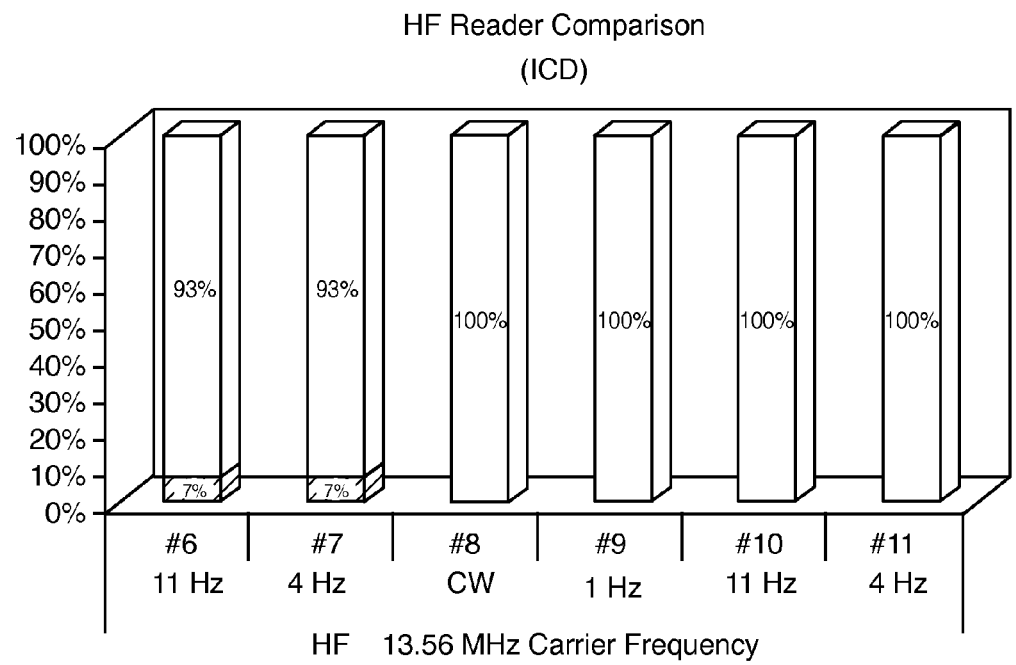
FIG. 26 is a chart similar to FIG. 25 except that it is a comparison of HF readers for ICDs.
Figure 28:
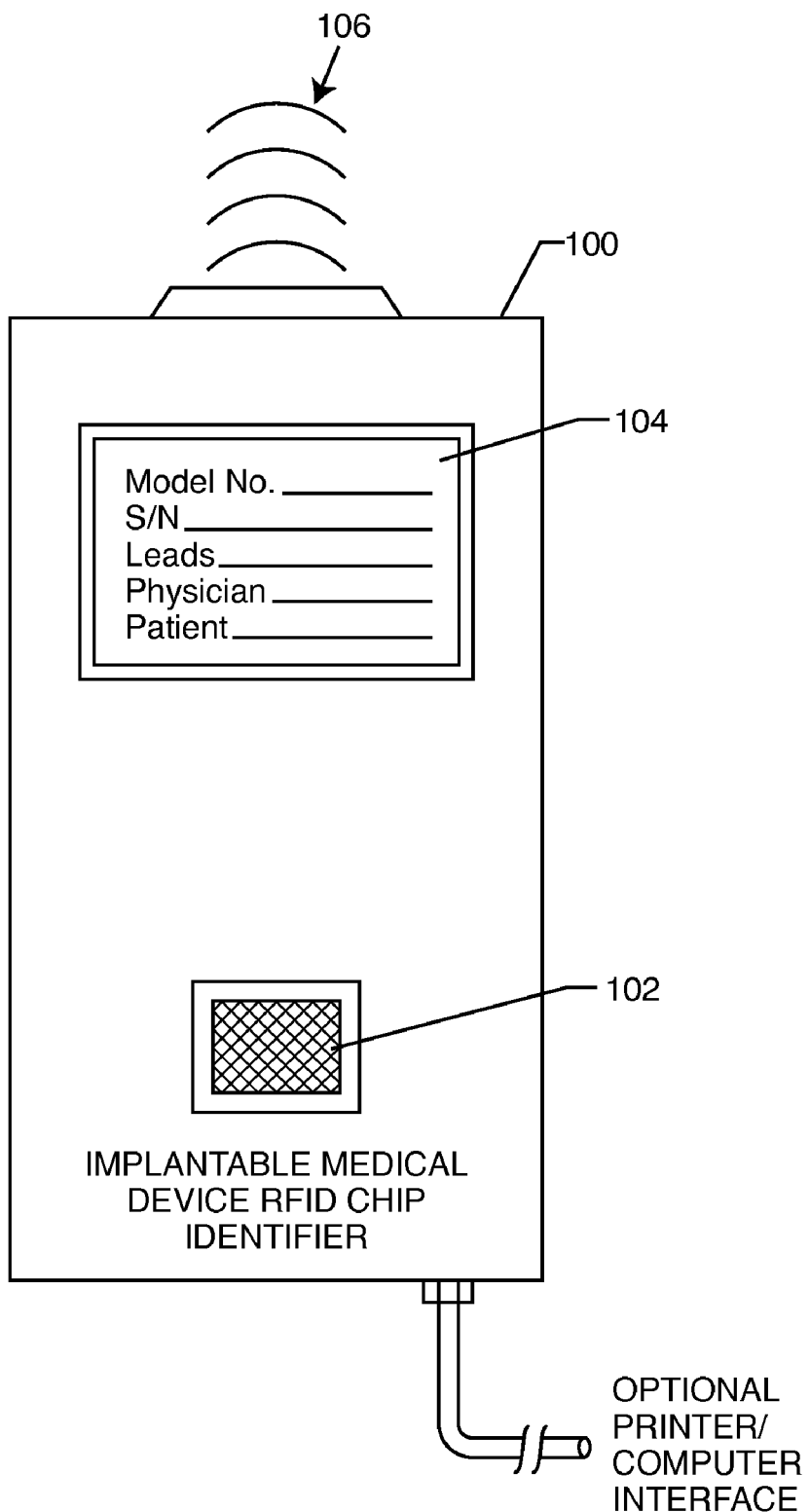
FIG. 28 is a schematic illustration of a novel RFID communicator system embodying the present invention.

FIG. 28 is the top view of a novel hand-held RFID reader/communicator 100 system of the present invention. Shown is a push button switch 102 and a display 104, which could display medical device model number, serial number, type and model number of leads, name and contact information for implanting physician, name and other pertinent information about the patient (with informed patient consent). The transmit pulses 106 are shown as a series of electromagnetic waves being emanated from the RFID reader 100. Optionally, the communicator 100 could include a printer, printer interface or computer/network connection for creating a permanent record. This would be advantageous for medical personnel at the scene, for creating accurate medical records and for future reference in case of medical, legal or other delayed concerns. The novel RFID reader of the present invention need not be hand-held as shown in FIG. 28. In fact, it could be mounted in a pedestal, in a desktop unit associated with an AIMD external programmer, mounted in the side of a building or door, or even in an automobile.

Figure 29:
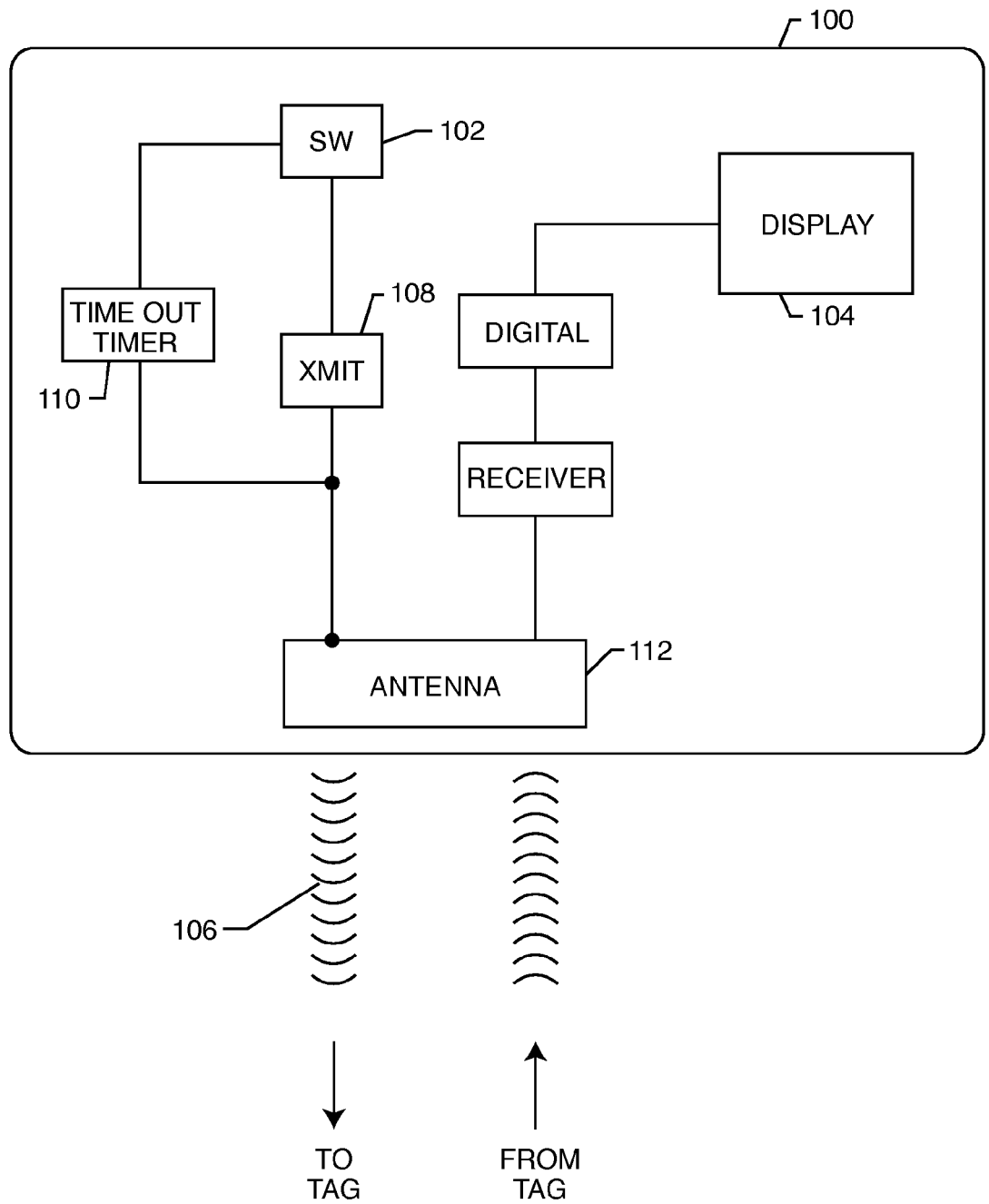
FIG. 29 is a functional block diagram showing a novel application of the present invention.

FIG. 29 is a functional block diagram showing a novel application of the present invention. Shown is the switch SW (102), which can be, but is not limited to, a push button switch like that shown in FIG. 28. In this case, the switch SW (102) would contain special electronic circuitry so it could transmit an electronic pulse 106 for no longer than 5 seconds, or other physiologically safe duration. In a preferred embodiment, the electromagnetic pulse 106 could have a duration or maximum transmit time of no longer than 0.5 seconds combined with a time-out period of 2 seconds or more. Depending on the type of patient AIMD, the transmit time can vary from nanoseconds to several minutes.

For example, for cardiac pacemaker, limiting transmit time to 0.5 seconds, would, by definition, make it impossible to have a Type 1 or Type 2 response from an implanted cardiac pacemaker or implanted defibrillator. As previously described, dropping of a few paced beats would not be detected by the patient and regardless, would be of no clinical significance. This approach provides an even greater safety margin for ICD compared with bradycardia pacing patient requirements as when implantable defibrillators sense rapid signals that could represent a dangerous ventricular arrhythmia, they begin to charge a high-energy storage capacitor. A final interrogation (sensing of biological signals) is made prior to delivery of the high voltage shock. This entire process takes at least 5 seconds and a progressively longer time as the ICD battery ages. Accordingly, by limiting the transmit pulse of the present invention to less than 5 seconds (preferably less than 500 milliseconds), one is guaranteed that no harm can come to the patient from malfunction or inhibition of a pacemaker or an implantable defibrillator, during transmission of important diagnostic information.

A similar corollary is made for all other types of neurostimulators. For example, consider the case of a cochlear implant. If one were to have a patient in an emergency room in a life threatening situation, the application of the reader of the present invention, would only cause the patient to hear some audible buzzes during the short burst from the RFID reader. For example, for an epilepsy control stimulator, one or two extra pulses to the brain would be of no clinical significance. The same would be true of a spinal cord stimulator, a vagus cord stimulator, an incontinence (bladder control) stimulator, or the like. Even if the short RF burst from the reader transiently terminated the output of a pain control stimulator, the patient would be without pain suppression stimuli a maximum of only 5 seconds. Therefore the present invention is applicable to all types of active implantable medical devices and is not just limited to pacemakers and implantable defibrillators.

Referring once again to FIG. 29, one can see that there is a timer circuit 110 designed to bypass the RF signal generator 108 within the RFID reader 100. After the transmit pulse 106 is sent to the RFID tag by antenna 112, which has been implanted inside a human or worn by a person in another RF signal sensitive location, the timer 110 prevents the switch 102 from working again for a predetermined amount of time, for example, at least 2 seconds. Therefore, if the push button switch SW (102) is held down continuously, only a single output sequence is delivered and a second and/or further outputs are suppressed until after the specified novel time-out or delay period(s) has occurred. No matter how long the switch 102 is activated and/or reactivated, the transmitter cannot continue to or continuously transmit an RF or any other type of electromagnetic signal. For example, applying the present invention to cardiac rhythm management devices, an optimal delay or time-out period would be in the range of 2 seconds, giving the heart, for example, time to revert to its intrinsic stable rhythm before it could be disturbed again by additional dropped beats if the reader were to retransmit. Of course, in patients with pacing capable devices, but without pulse generator dependent rhythms, for example, during normal sinus rhythm, the reader transmissions would have no effect even when the switch was appropriately activated. On the other hand, in ICD patients, whether paced or in a normal intrinsic rhythm, there would also be potential risk during RF reader activation, in particular, as transmission durations reach and exceeded ten seconds.

Figure 30:
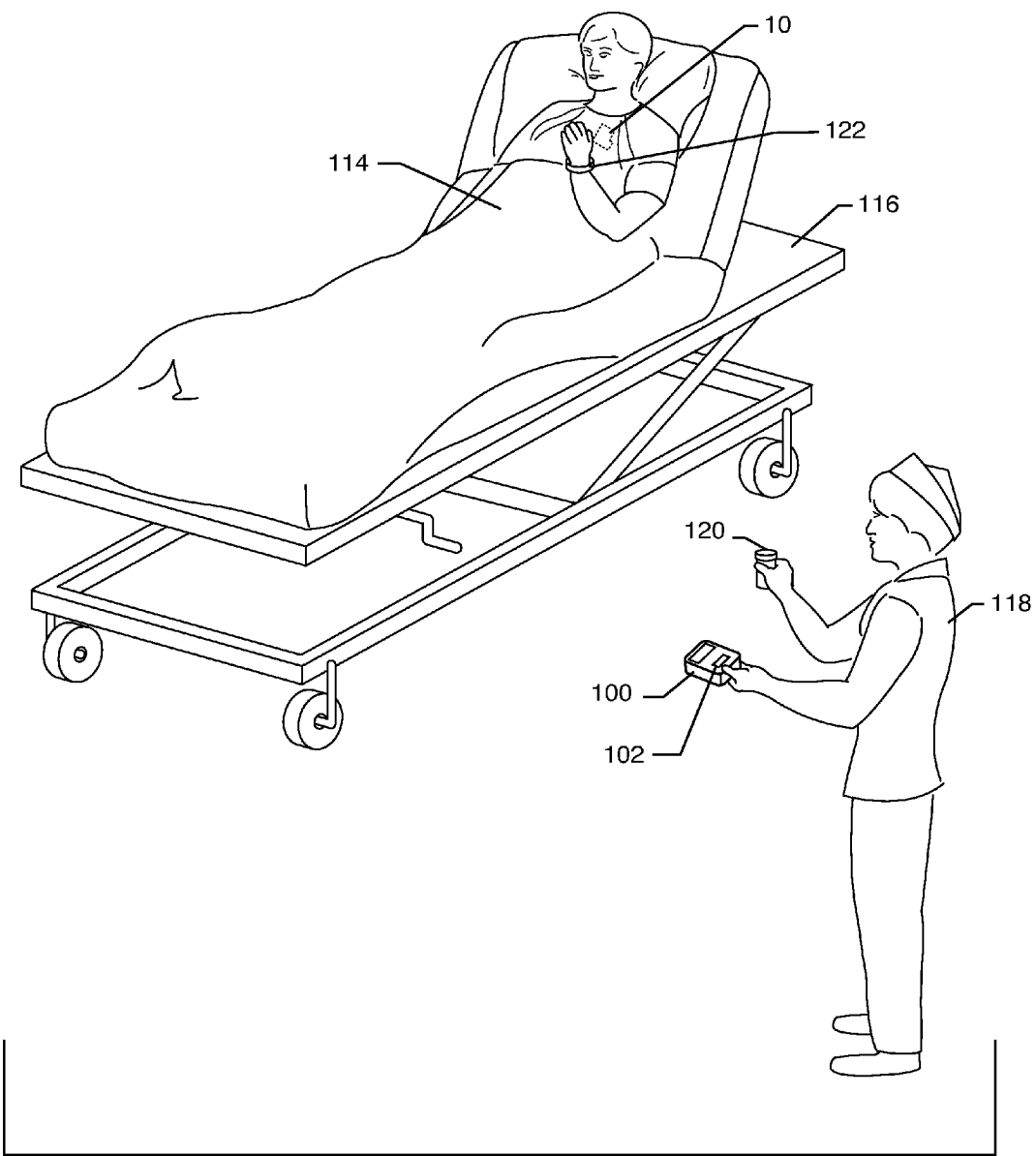
FIG. 30 is a diagrammatic perspective view of a patient wearing an RFID-enabled bracelet, and a nurse providing medication to the patient and utilizing the RFID communicator of the present invention.

FIG. 30 is an illustration of the evolving use of RFID readers and associated tags in hospital environments. A patient 114 is shown laying in a typical hospital bed 116 with a nurse practitioner 118 entering with medication 120 from the hospital pharmacy. The nurse also has an RFID reader 100 in her hand. Upon giving the drugs (injection or pills or IV) to the patient, the nurse will use the RFID reader 100 to interrogate a special hospital wristband 122 which is affixed to the patient's arm. This wristband has an embedded RFID chip and associated antenna, which together form an RFID tag. In this way, the hospital's computer system will have an exact record of the time that the medication was dispensed into exactly which patient.

There are a number of other rapidly evolving applications for hospitals. For example, RFID readers have been strategically placed in several test hospitals in the United States where the readers are embedded in hallway portals. As the patient is wheeled on a gurney or portable hospital bed through the hospital, each time the patient passes through one of these portals, his or her unique RFID patient wristband tag will be read so that the location, date and time will be recorded. Such a system can also be used for tracking of hospital equipment, surgical supplies, and the like. There are also emerging applications for RFID reader systems in the operating room environment. Not only tracking of equipment and associated surgical supplies is important, but it's also very important before a patient is closed up after an operation that nothing be left behind. In certain new particular operating room applications, each surgical sponge has an RFID tag affixed to it so that at the end of the operation an RFID sponge reader is moved over the top of the patient surgical field to detect if any RFID-tagged sponges are still inside the body before final closure is made. One can see that in these RFID reader-rich environments, the medical personnel would not necessarily be aware that the patient had an active implantable medical device (AIMD) such as cardiac pacemaker, which could be adversely affected by the electromagnetic signal of the LF and HF RFID communicator.

Referring once again to FIG. 30, the nurse 118 is holding an RFID reader 100 that has a transmit button 102. The nurse 118 is also holding a container of pills (pharmaceuticals) 120 to be dispensed to the patient 114 lying in hospital bed 116. Said patient is wearing an RFID tagged wristband 122 as has been previously described, and has a pectorally implanted pacemaker AIMD 10. When the nurse gets close to the patient, she holds the RFID reader 100 close to the patient wristband 122 and depresses button 102. If the transmit time is limited in accordance with the present invention, e.g. to less than 0.5 seconds (500 milliseconds), then at most a pacemaker patient will only drop a few heart beats. However, the time-out circuit is equally important. If for some reason the nurse pushed the transmit button 102 over and over again, this could cause a prolonged pacemaker inhibition period which could be potentially pro-arrhythmic or even life-threatening to the patient. The novel time-out circuit of the present invention ensures that the transmit button 102 will not work again for a specified period of time.

For pacemaker and implantable defibrillator applications, the ideal time-out period is based on a number of factors. For a cardiac pacemaker, that has to do with the wide range of human conditions and their particular underlying cardiovascular disease or cardiac hemodynamics. Taking all of this into consideration, the preferred transmit time is 500 milliseconds or less and the preferred time-out period is two seconds or longer. This preferred embodiment is also ideal for implantable cardioverter defibrillators, which in order to deliver therapy, must first detect a dangerous (fast rate) ventricular arrhythmia. If such fast rate ventricular arrhythmia is detected, the ICD high energy internal storage capacitor is charged up. It typically takes several seconds for the battery to charge up the capacitor. Then the ICD reinterrogates to see if the dangerous arrhythmia is still present. If it is, the ICD delivers a high voltage shock. This entire process generally takes longer than 6 seconds. This preferred embodiment also works in general for neurostimulators.

It has been widely described in the literature that when potential patients have a resting heart rate below 40 beats per minute that they become a candidate for a cardiac pacemaker. It is also a fact that almost all pacemakers that are built today are sent out with factory default settings of 60 beats per minute. Of course, this setting can be adjusted through re-programming by the implanting physician (often working in cooperation with the manufacturer's device representative). In certain cases, for world class athletes, the physician may decide to turn down the pacemaker set rate to as low as 50 beats per minute, for example. This is because certain athletes find 60 beats per minute to be uncomfortable (rate too fast). In a preferred embodiment of the present invention, the total transmit time of the electromagnetic signal would be limited to 500 milliseconds (0.5 seconds). This would be combined with a time-out period of 2 seconds or more. If one does the math over a full minute, this would mean that a pacemaker dependent patient that was being paced at 50 beats per minute would lose, at maximum, 10 beats over that full minute or have an effective 40 beats per minute heart rate. This would put the patient right on the edge of the indications for a cardiac pacemaker. However, this still provides a high degree of safety for an athletic patient, since it is well known that athletes can drop to as low as 25 beats per minute before they become dizzy. Accordingly, the preferred embodiment of the present invention would be to limit the total transmit time to 500 milliseconds and the time-out period to a minimum of 2 seconds. This preferred embodiment also works well for ICD and neurostimulator patients.

However, the present invention does not limit the transmit time and time-out period to any specific number. The reason for this is there is great variability in the characteristics of AIMDs. For example, AIMDs are evolving over time. For example, pacemakers are evolving to have more functions and more lead-based sensors. Accordingly, their EMI characteristics could change over time necessitating that the total transmit time and/or the time-out period be adjusted over time. In addition, it's quite possible, if not likely, to interrogate, with an RFID reader, a pacemaker and in the same patient, then later interrogate, for example, a spinal cord stimulator. This is particularly true for LF chips that may be embedded inside the AIMD housing. The read range of these RFID readers is typically from 2 to 6 inches maximum. This would place the RFID reader in very close proximity to the AIMD that had an RFID tag associated with it. Accordingly, one could conceive of a reader that was used only for interrogating pacemakers when it was closely held. In this case, it would have to have a more limited transmit time and perhaps a longer time-out period. On the other hand, if one were interrogating a spinal cord stimulator, the transmit time and time-out period would not be nearly as critical because the spinal cord stimulator is not a lifesaving device. In other words, if the patient experienced a few seconds of pain, this would be far preferable than having the heart stop.

The transmit time is, of course, also related to the amount of information that is desired to be either written or retrieved from a tag. Accordingly, in the simplest embodiment, a transmit period of only a few nanoseconds may suffice. This would work in combination with a look-up table that would be built within the reader. In this case, all the implantable medical device, such as a cardiac pacemaker, would have to transmit would be a two-letter code. This two-letter code would ideally be tied to an Association for the Advancement of Medical Instrumentation (AAMI) standard or International Standards Organization (ISO) standards wherein the manufacturers look-up tables would be contained. For example, the code A1 could stand for St. Jude Medical. It would only take the tag a few nanoseconds to transmit the code A1. On the other hand, if it were desired that the tag transmit not only manufacture, but in addition, model number, serial number, date of manufacture, name of both the patient and implanting physician and so on, then the data transmission time would increase. Accordingly, in the present invention, the transmission time would be limited, in general, from 1 nanosecond all the way to 2 seconds, and the time-out period can be from a few nanoseconds to a number of minutes. As mentioned, this is very device specific as well. A drug pump will not respond nearly the same way as a cardiac pacemaker, for example.

Figure 31:
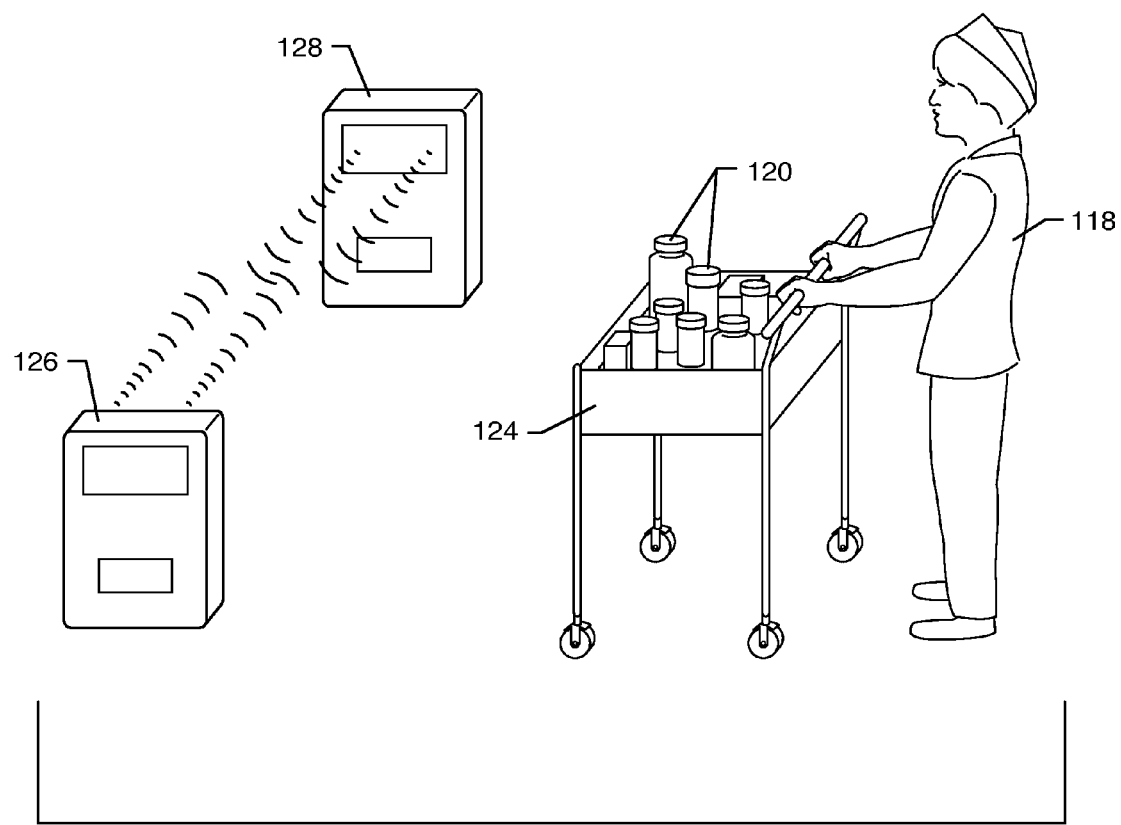
FIG. 31 is a diagrammatic perspective view of a medical assistant passing medications through an RFID portal or zone incorporating the present invention.

FIG. 31 illustrates a hospital nurse 118 who is pushing a cart 124 which is loaded with various pharmaceuticals 120. As she exits the pharmacy, RFID pedestal, gate, or door readers 126 and 128 scan the pharmaceuticals 120, which all have an attached or embedded RFID tag (not shown). In this scenario, no hospital patient is present. However, the nurse 118 herself could be a pacemaker patient. If she were to linger in the RFID field between the readers 126 and 128, she could be subject to a life-threatening Class 1 response. Accordingly, the RFID readers 126 and 128 have a limited transmit time and a time-out period in accordance with the present invention.

Figures 32, 33:
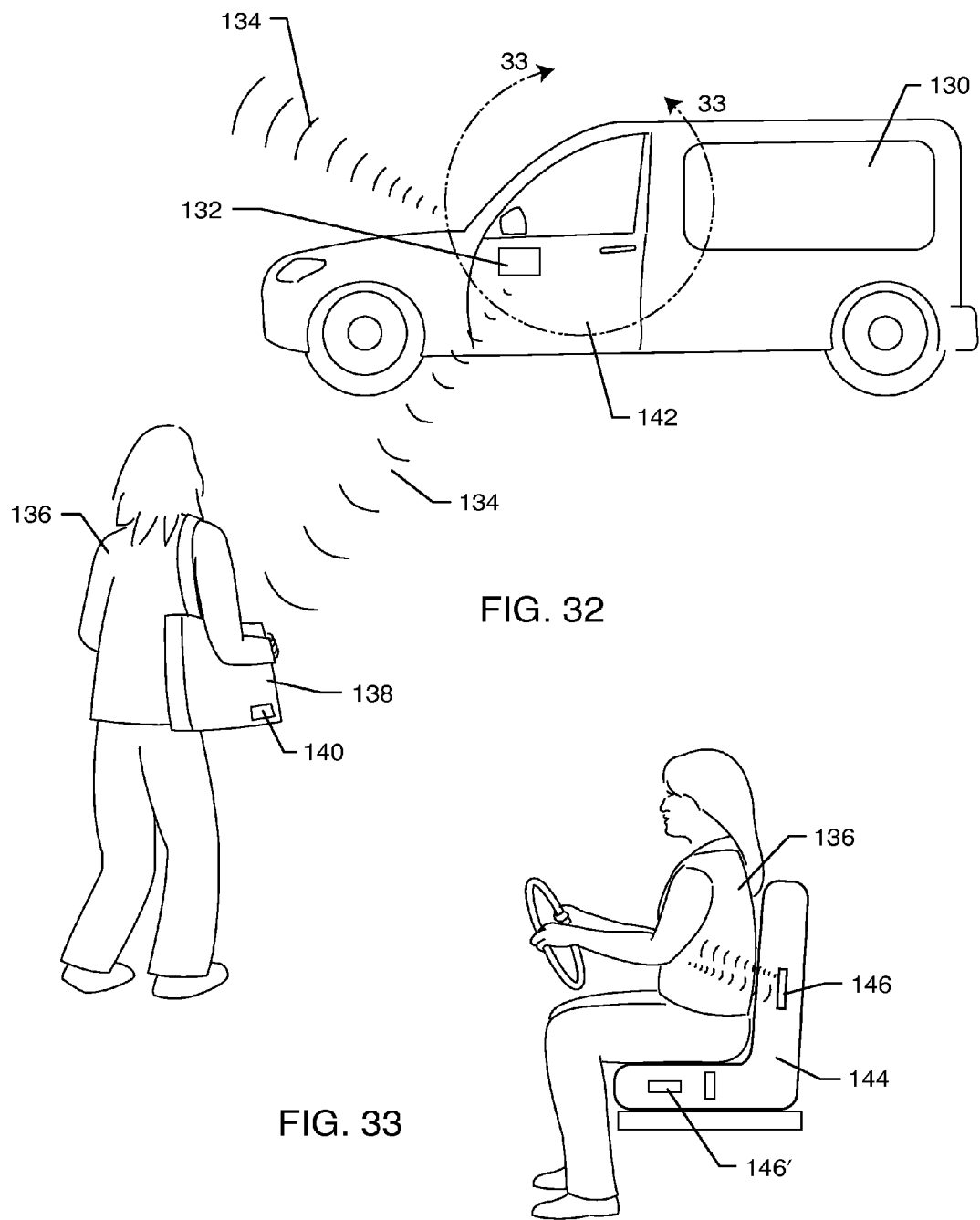
FIG. 32 is a perspective view illustrating a driver approaching a vehicle enabled with RFID keyless entry incorporating the present invention.
FIG. 33 is a diagrammatic side view of the driver seated within the vehicle, having an RFID security system embedded within the seat incorporating the present invention.

FIG. 32 illustrates a completely different situation—a newly emerging type of keyless entry system for automobiles. Shown is a sport utility type automobile 130 with an RFID interrogation system. While parked, the automobile has a built-in RFID reader 132 that sends out RFID transmission pulses 134 in all directions on a regular basis searching for a correct RFID tag (key) that may come into its vicinity. In FIG. 32, the automobile 130 is being approached by the owner 136 who is carrying a purse 138. Inside of the owner's purse 138 is her special automobile RFID tag 140. When the car senses the presence of tag 140 it will go into a more active RFID interrogation mode. As the driver 136 approaches the car door 142, after detecting and reading the correct tag 140, it will automatically open or unlock. This is different from the key fobs that most people are familiar with where you have to push a button to open or lock the car. In this case, the driver 136 never has to take the tag 140 out of her purse (or other location on or near her body). The automobile 130 simply senses it.

There may also be an antitheft feature associated with automobile 130 that is better illustrated in FIG. 33. Once the driver 136 enters the car 130 and sits down in the driver side seat 144, as illustrated, a reinterrogation is made by a different RFID reader transmitting antenna 146 embedded in the seat back. In some cases, this interrogator antenna 146 can alternatively also be in the seat underneath the driver. In this way, the RFID system of the vehicle 130 validates that the correct tag 140 is actually inside the car 130 and will start the ignition and allow the car to be driven.

However, this also puts a potential pacemaker patient 136 (the driver or passenger) in very close proximity to an RFID transmitting antenna 146. This is certainly well within the threshold distances measured by the recent FDA study which, for example, could inhibit a pacemaker. FIGS. 32 and 33 show that many RFID systems are completely hidden from view. In other words, a friend of the driver who may be a pacemaker patient could enter this environment and not even be aware that this was an RFID enabled vehicle. Furthermore, the driver 136 of the vehicle 130 who offers to give a friend a ride may not even be aware that the friend is a pacemaker patient. In other words, due to the explosion of RFID readers/communicators in so many different environments, it's really not appropriate to consider the FDA "don't lean/don't linger" admonition for retail store EAS gates to be effective in all cases. Also, signage is very impractical. Obviously it would be very undesirable to paint on the outside of your automobile that this is a danger to pacemaker patients because this is an RFID enabled vehicle. Accordingly, there is a need in the automobile situation described in FIGS. 32 and 33 and equivalent situations where RFID reader interrogators are invisible to the patient, for these systems to be designed in accordance with the present invention with a limited transmit time and a time-out period.

Figure 34:
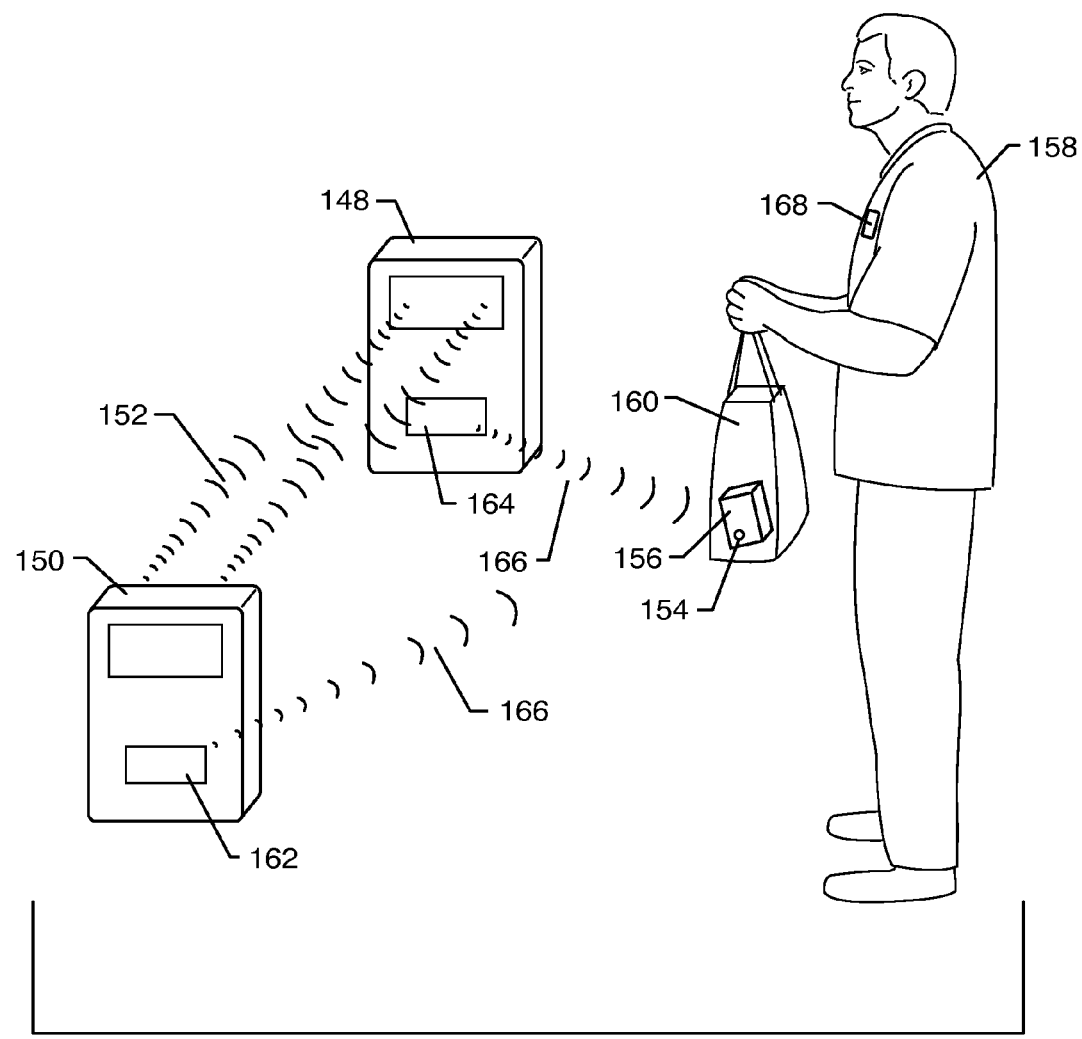
FIG. 34 is a diagrammatic perspective view of a shopper having purchased articles having RFID identifying tags associated therewith and passing through a RFID security gate embodying the present invention.

FIG. 34 illustrates a pair of electronic article surveillance (EAS) gates 148 and 150 as are well known in the prior art. These are typically made by companies such as Sensormatic and others and operate at 58 kHz, providing a continuous high-powered pulsing electromagnetic field 152 which can activate an RFID tag 154 located on an retail article 156. An example is shown with the shopper 158 who is holding a shopping bag 160. Inside the shopping bag is a book or a DVD 156 which has an embedded EAS tag 154. If the tag 154 has been properly deactivated by the cash register clerk, it will not be activated by the EAS field 152 and emit a return pulse. Therefore, in this particular example, the shopper can exit the retail store without setting off an alarm. In the case where the shopper is a thief or the tag has not otherwise been properly deactivated, then the tag would set off the alarms of the EAS gate system. In accordance with the present invention, the EAS gates 148 and 150 are also combined with an RFID reader/interrogator 162, 164, which sends out an RFID interrogation pulse 166. If the shopper 158 happens to be a pacemaker patient whose pacemaker 168 contains its own RFID chip (not shown), the RFID reader of the EAS gate will detect the presence of a pacemaker and then shut down the powerful EAS gate fields such that it cannot interfere with the cardiac pacemaker. Of course, the RFID readers 162, 164 that are incorporated within the EAS gates 148 and 150, will have to incorporate the novel limited transmit time and time-out feature of the present invention.

An RFID reader, such as illustrated in FIG. 34, can also be used to track a high volume of human traffic. For example, one entering a major sports stadium may have a ticket that has an RFID tag within it. There is also shopping associated with this activity, such as purchasing items such as sportswear or memorabilia. These could have EAS anti-theft tags associated with them. Because of the high volume of traffic, it would be undesirable to turn off the EAS gates. It would also be undesirable to have the RFID reader have a limited transmit time or too long of a timeout period. This is because of patrons streaming through the gates as the RFID reader was interrogating the tag embedded within their ticket stubs. Tags could be missed during the time-out period of the present invention. Accordingly, it is a feature of the present invention that the continuously transmitting RFID reader that is associated with an EAS gate would detect the RFID tag within a pacemaker patient (or other type of AIMD patient) and then go temporarily into a limited transmit and timeout period mode so that the pacemaker patient can safely pass through the portals.

Figure 35:
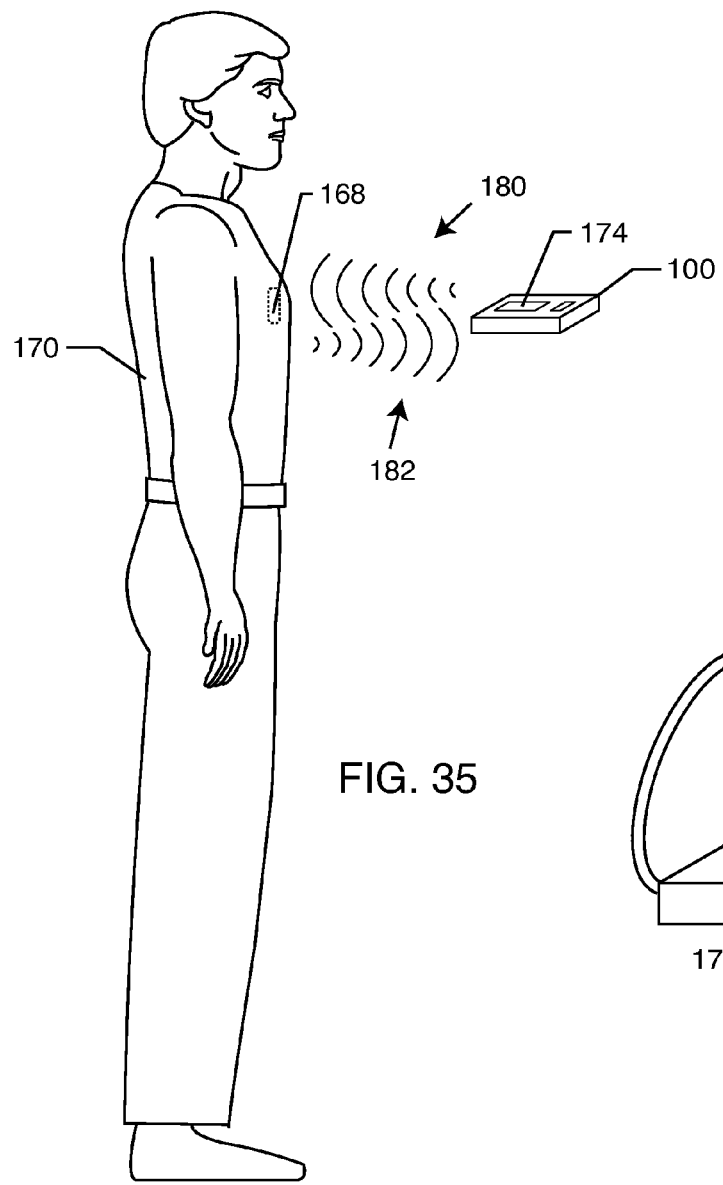
FIG. 35 is a depiction of a patient with an AIMD fitted with an RFID tag communicating with an external interrogator/reader embodying the present invention.

FIG. 35 illustrates a patient 170 with an implanted pacemaker 168. There is a great need in ambulances, hospital emergency rooms, and other environments to quickly and accurately detect the model number, the serial number and other information about any implanted medical device. This is also very important before certain diagnostic procedures such as MRI. Referring once again to FIG. 35, the RFID reader 100 can also incorporate a barcode reader 174.

Figure 36:
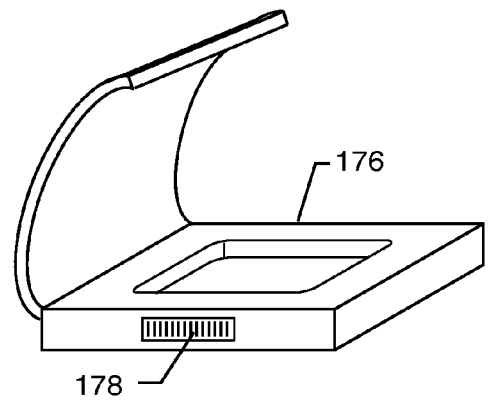
FIG. 36 is a perspective view of an exemplary sterile package used to hold an implantable device, having a tracking barcode associated therewith.

FIG. 36 illustrates an opened sterile package 176 that was previously holding the cardiac pacemaker 168 of FIG. 35 which is now inside the patient 170 shown in FIG. 35. In the operating room, the sterile box is opened and then a barcode 178 on the side of the packaging is read by the RFID reader/writer 100. After implantation into the patient, the RFID reader/writer is used to write to the tag associated with the pacemaker 168 (before or after implantation into the patient) so that the model number, serial number and other information pertaining to the cardiac pacemaker 168 is stored permanently on its RFID chip. This is shown with the communicator unit 100 sending a signal 180 towards the pacemaker 168 and its associated RFID tag (not shown). The RFID tag could return a signal 182 to confirm receipt and storage of the information, or any other additional information sought by the reader 100. This facilitates entry and storage of data onto the chip associated with the cardiac pacemaker in such a way that it is free of errors. In this regard, doctors are notorious for opening the packaging and throwing it away without properly filling out information. In accordance with the procedure described above, it makes it very easy to for the medical personnel to simply swipe the barcode reader 174 and then, by pushing a transmit button, store the final information on the RFID chip associated with the patient pacemaker 168.

Ideally, the medical device manufacturer would have a special RFID reader associated with their manufacturing line. For example, a cardiac pacemaker manufacturer, at the point of final sterilization and packaging, would use a production line barcode reader-RFID writer to read the barcode 178 associated with the production lot traveler or packaging 176 and then this production line RFID writer would write this information to the tag that is embedded in or associated with the pacemaker or other medical device. This would go into an area of permanent memory on the RFID tag. There would also be an area of volatile memory that the doctor could optionally use later to enter information about the patient, the patient's medical condition or even information about the implanting physician all at the time of implant. This would typically be done with informed patient consent. Of course, these principles are applicable to any external or internal medical device. Moreover, the RFID chip associated with the AIMD need not be embedded within the header block or the housing of the AIMD. The RFID tag could also be implanted in other locations within the patient's body or even within a special patient ID card.

In summary, FIGS. 35 and 36 illustrate yet another scenario in which RFID tags will soon be placed in AIMDs, and readers will be deliberately be brought very close to the patient in order to identify information about the AIMD itself. The situation illustrated in FIG. 35 is probably the most dangerous, for a pacemaker or ICD patient. In this example, a very powerful RFID reader is deliberately placed literally right up against the patient's chest in order to retrieve information from the pacemaker or ICD itself. Obviously, it would be highly undesirable if EMI from the reader interrogation signal disrupted the proper operation of the AIMD. Accordingly, it is critical that this RFID reader/interrogator have a limited transmit time and time-out period of the present invention.

Figure 37:
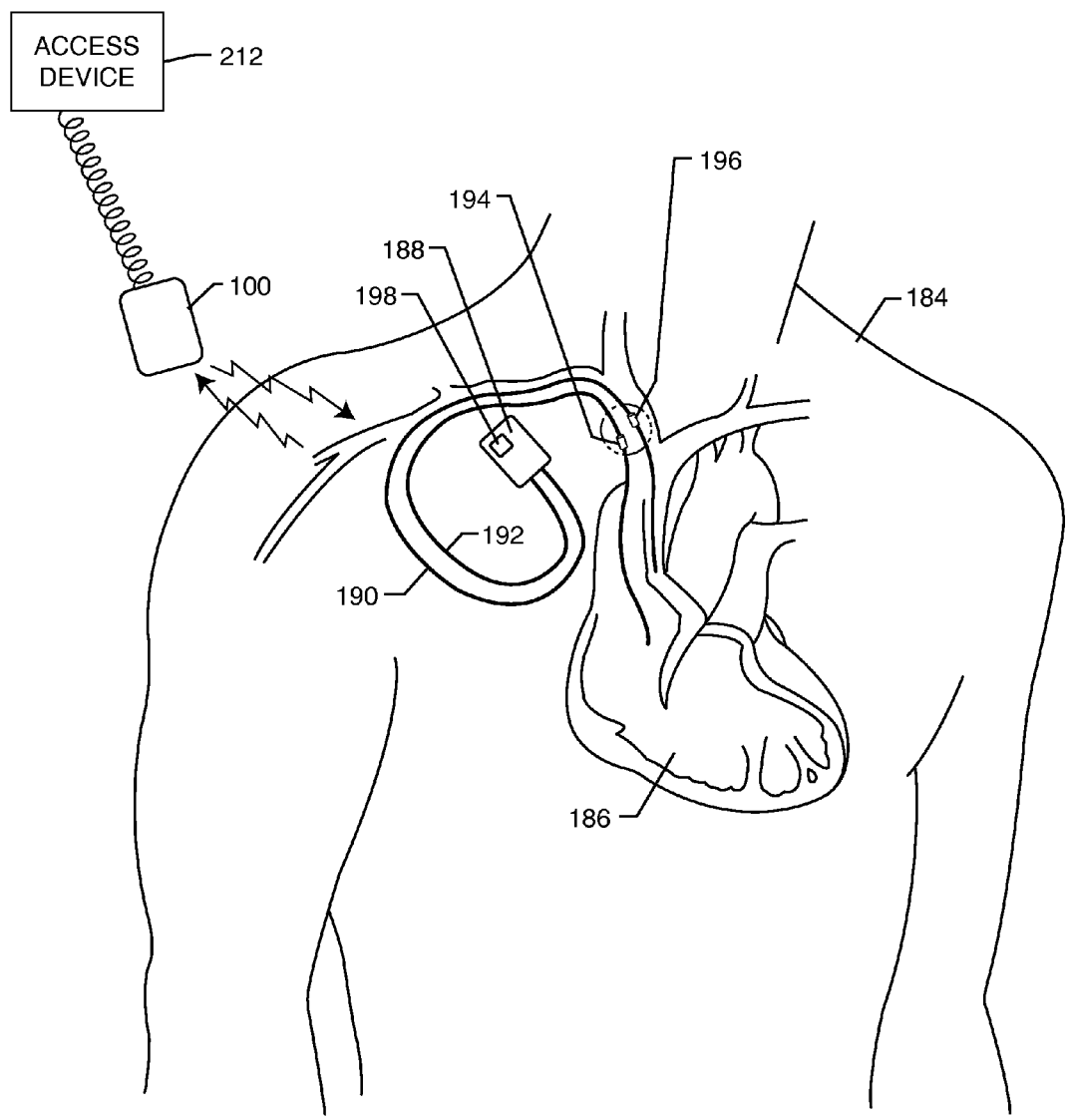
FIG. 37 is a perspective and somewhat schematic view of an active implantable medical device (AIMD) including leads directed to a heart of a patient, and an interrogator and access device for reading information from RFID tags associated with the leads and/or AIMDs or other implanted monitoring, diagnostic or therapeutic devices.

FIG. 37 shows a pictorial diagram of the heart 186 of a patient 184 who has an implanted medical device 188, such as a cardiac pacemaker. Leads 190 and 192 are routed into the right atrium and right ventricle respectively. There are optional suture tags 194 and 196 that are affixed to the leads 190 and 192 which can contain RFID tags of the present invention. The RFID tags that are associated with the leads can be used to identify the manufacturer and model number of the leads and also the MRI compatibility. The pacemaker 188 can also have an RFID tag 198 associated with it in accordance with the present invention. An RFID access device 212 is integrated to an RFID reader 100, as illustrated.

Figure 38:
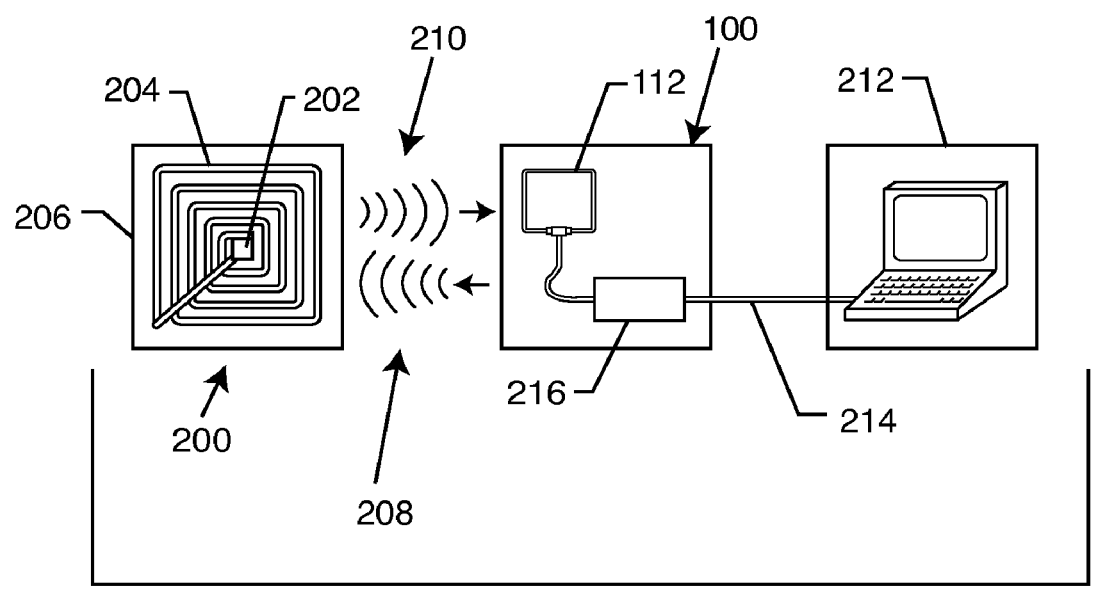
FIG. 38 is a block diagram depicting operation of a system including the RFID tag of the present invention.

With reference to FIG. 38, an exemplary RFID tag 200 is shown, which could represent the RFID tag disposed in suture tag 194 or 196, or the RFID tag 198 embedded within the AIMD 188 of FIG. 37. As is well known in the art, the RFID tag 200 includes an RFID chip 202 conductively coupled to an antenna structure 204 and disposed on or within a substrate base 206. The RFID tag 200 can communicate with the reader/interrogator communicator 100, which may have an antenna 112 embedded therein or otherwise associated with it. The communicator 100 sends an RFID pulse or signal 208, which activates and causes the RFID tag 200 to return a signal 210. This signal, and accompanying data, is received by antenna 112 of the communicator device 100, and this data may be saved within the communicator device 100, displayed on a display of the communicator device 100, as previously described, or sent to an access device 212, which may be in the form of a desktop, laptop computer, computer system or the like. This can be done in real-time, or the communicator device 100 can later be plugged into the computer system 212, such as by means of cable 214 extending between the computer 212 and a port 216 of the communicator device 100. In this manner, the data may be immediately transferred to the computer system 212, or may be later downloaded to the computer system 212.

The RFID reader 100 is capable of sending out a transmit pulse and receiving return signals from the RFID tags previously described within the patient. In the case where there is no return pulse, in the present invention the display will automatically read, "no tag detected" or something similar. In an emergency room situation, it is expected that as one gets a "no tag detected" reading, one would move the reader very close to the patient's implanted device and attempt to reinterrogate. If one again sees a "no tag detected" display, then one would have to assume that they have an old (legacy) device that does not have an embedded RFID tag. Under these circumstances, one would have to return to the old time-consuming routine of searching around the hospital for an interrogator programmer compatible with the implanted medical device.

Another non-medical example of RFID tracking of individuals, devices, supplies, etc. that could have serious clinical consequences occurs in hospitals. For example, cross corridor patient and object transit detectors are increasingly in use. The potential for an intermittently or regularly device dependent patient to be "parked" in this area is obvious and the need for limited duration transmit pulses plus time-out periods are also obvious. Without question, the use of traffic monitoring electronic gates will increase and potentially become universal not only in hospitals, but also in military, security and important commercial establishments and endeavors.

Figure 39:
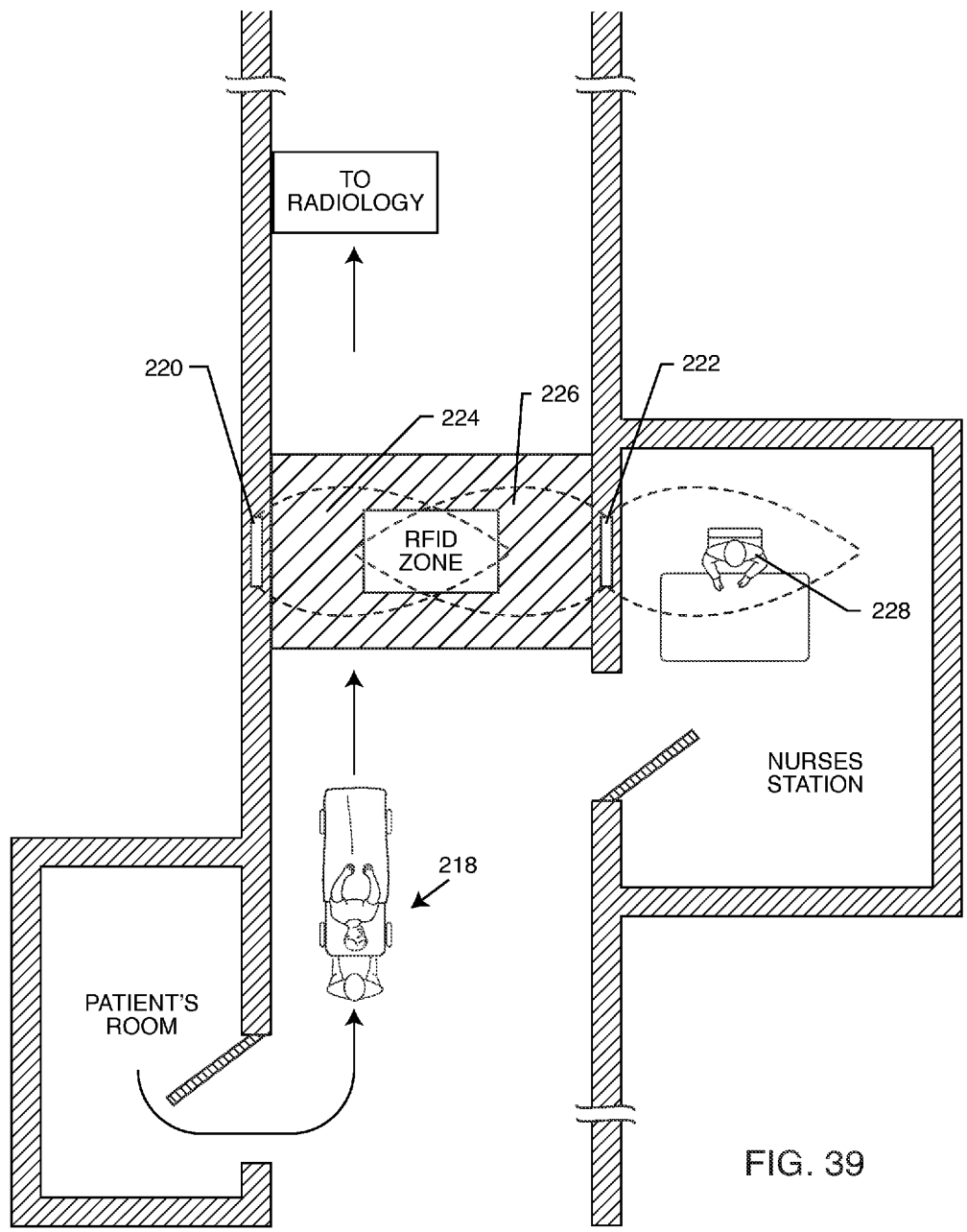
FIG. 39 is a schematic illustration of a medical facility illustrating a patient being moved from his room past a nurses' station and to the radiology department so as to pass through an RFID zone created by RFID communicators, in accordance with the present invention.

FIG. 39 shows a typical hospital corridor along with a nurses' station and a patient room. A hospital orderly is pushing a patient who is on a wheeled bed/gurney 218 down the hallway in the direction of radiology. There is an RFID zone, which can be labeled in a number of ways including signage, stripes on the floor, etc. It will be obvious to those skilled in the art that any number of means of identification, including bumps or a different type of a floor texture could even be used. The RFID zone has a number of multiplexed RFID reader antennas. In this case, two RFID readers, 220 and 222 are shown. However, they could also be embedded in the floor and ceiling. The idea is that we have overlapping RFID fields 224, 226, such that it would not be possible for the patient who is wearing an RFID wristband to go through the zone undetected.

The purpose of such a system is to track the patient through the hospital so that this information is entered into the hospital's computer system. This allows doctors and other medical personnel to always know where a patient is. The same also applies to important pieces of hospital equipment.

As previously mentioned, UHF readers are not particularly desirable for detecting humans because of the affect of body tissue and water to reflect and/or absorb such short wavelength signals. Accordingly, in the preferred embodiment, the RFID readers 220 and 222 are of either low frequency (LF) or high frequency (HF) protocols. Hospital corridors are quite wide in the range of 15 to 20 feet. The read range for both LF and HF is not sufficient that a single reader could properly cover the full corridor width. Accordingly, this is why portals are used that involve a number of multiplexed readers. UHF readers typically have back plane plates so that they have a very high front-to-back transmission ratio. That is, they transmit energy very effectively in the forward direction and very little signal would be found behind them. This is not true, particularly for LF readers as illustrated in FIG. 39. The front-to-back ratio of these large loop antennas is approximately equal.

There are several dangers associated with the schematic of FIG. 39, which are all solved by the present invention. First of all, in the nurses' station, a nurse 228 is inadvertently sitting in the back plane radiation of RFID reader 222. She may sit in this position for hours. If the nurse or technician happens to be a pacemaker patient, this would place the patient in the presence of the RFID reader for prolonged periods of time. Accordingly, it is a property of the present invention that such RFID readers 220 and 222 have a limited transmit time and a suitable time-out period such that the person who may themselves be a pacemaker or ICD patient in the nurses' station or other office not have a dangerous Class 1 response. The same is also true of the patient on the wheeled bed 218 who could also be a pacemaker/ICD patient. If the patient were inadvertently parked in the RFID zone for a prolonged period of time, the RFID fields could inhibit the pacemaker of a pacemaker dependent patient. This, of course, could be life-threatening.

However, in accordance with the present invention, RFID readers 220 and 222 both have a limited transmit time and a time-out period, such that this could not be life-threatening to the patient 218 or the nurse 228. Because the RFID readers have a limited transmit time and a time-out period, the RFID zone may be labeled so that the hospital orderly will deliberately delay and allow the patient to be in this zone for a predetermined period of time, such as at least ten seconds. This is so that the patient's tag is not missed during RFID reader interrogation. If the orderly were to push the patient's bed rapidly through the RFID zone, it is possible that the patient could transit this zone during the time-out period and therefore, the patient's tag would not be read.

Figure 40:
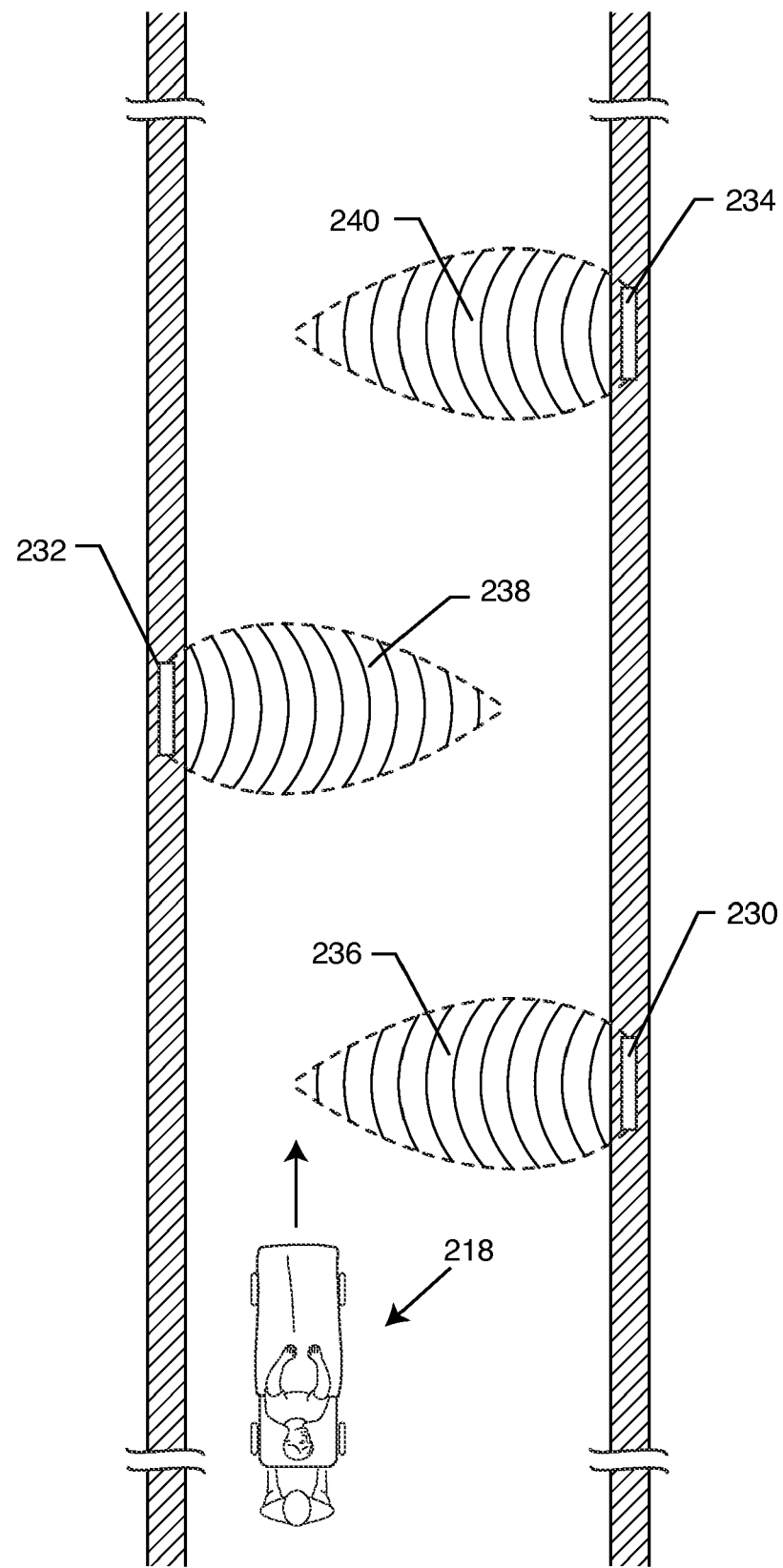
FIG. 40 is a schematic illustration similar to FIG. 39, wherein the RFID communicators are staggered throughout the corridor.

FIG. 40 illustrates an alternative arrangement of the hospital corridor of FIG. 39 wherein it would not be necessary for the orderly to delay. In this case, the RFID readers 230, 232 and 234 are staggered. Their fields 236, 238 and 240 do not overlap; however, it would be highly unlikely that the orderly would snake his way through these fields. It is much more probable that he would go in a straight line and therefore, it would be extremely unlikely that the patient's RFID tag would fail to be read. Although the patient 218 could be exposed to an RFID field for a prolonged period of time in such an arrangement, the RFID readers 230-234 incorporate the limited transmit time and time-out period of the present invention, such that the patient would be at no risk from the RFID fields 236-240.

Figure 41:
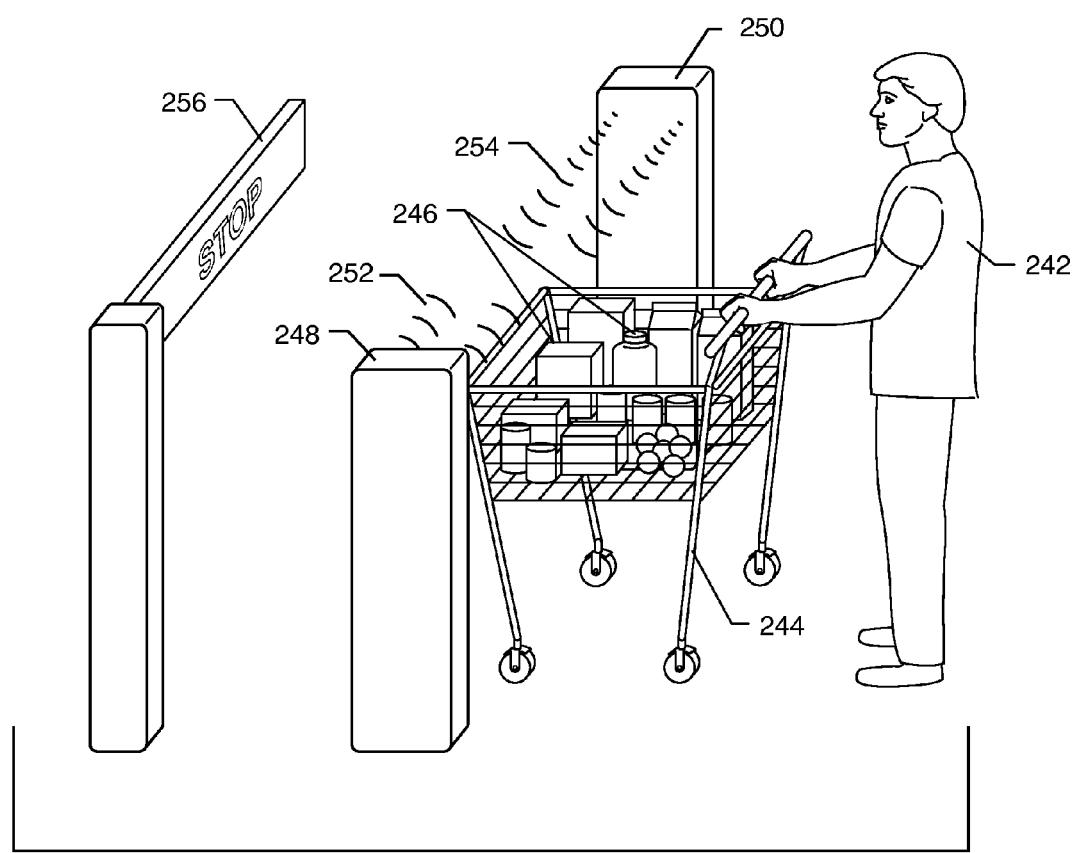
FIG. 41 is a perspective diagrammatic illustration of a shopper with a cart having articles to be purchased therein, and passing through an RFID checkout portal incorporating the present invention.

FIG. 41 illustrates another application for RFID readers that is emerging, in the form of a modern state-of-the-art supermarket automated checkout station. In this case, a shopper 242 is leaving a grocery store with a shopping cart 244 full of items 246 that he intends to purchase. Each of the items is tagged with an appropriate RFID tag (not shown). As illustrated, the shopper must pass between the RFID readers 248 and 250, which are transmitting signals 252 and 254 at a continuous and rapid rate, such that they will pick up all of the items 246 in the shopping cart 244 and immediately present a bill. As soon as the shopper's credit card is read, he will receive a print out of the bill and be ready to go.

Obviously, if the shopper 242 happens to be a pacemaker or ICD patient, the pacemaker could possibly have a Type 1 response which would possibly present a life-threatening situation. It is not even necessary that the shopper have a shopping cart with RFID tags. Since the readers 248 and 250 are continuously looking for tags, they are continuously emitting a signal. Accordingly, if a pacemaker patient entered the store and decided not to buy anything or to go back to his car and exited, his pacemaker would be exposed to the fields continuously transmitted from these same RFID readers 248 and 250. This becomes particularly problematic if the shopper/pacemaker patient were to linger in the presence of the field. This, in fact, has happened in the past with electronic article surveillance (EAS) gates typically operating in the 58 kHz range. There are documented cases of pacemaker malfunctions, inappropriate ICD high voltage discharges and the like. This led to the FDA's admonition to all pacemaker and ICD patients to "don't lean/don't linger," which generally does not work for the RFID reader industry. However, for the grocery store example illustrated in FIG. 41, the RFID pedestals 248 and 250 are obvious and could be seen and readily recognized by a pacemaker patient.

Referring once again to FIG. 41, one can see that it is necessary that the RFID reader interrogators 248 and 250 have a limited transmit time and time-out period of the present invention. This is very important in the case where the shopper 242 has a pacemaker or ICD. However, because of the limited transmit time and time-out period, if the shopper were to go quickly through the reader pedestals, all of the items 246 in his shopping cart 244 may not be read and properly costed. Accordingly, there is some sort of a stop gate 256 or other feature which requires the shopper to linger for a sufficient time in the field such that all of the items and articles 246 are properly read. Once the cash register receipt is printed and the shopper has paid, then the gate 256 would automatically lift so that the shopper can exit the store. It will be obvious to those skilled in the art that any number of types of gates or doors or even the presence of a monitoring person can all accomplish the same effect.

Figure 42:
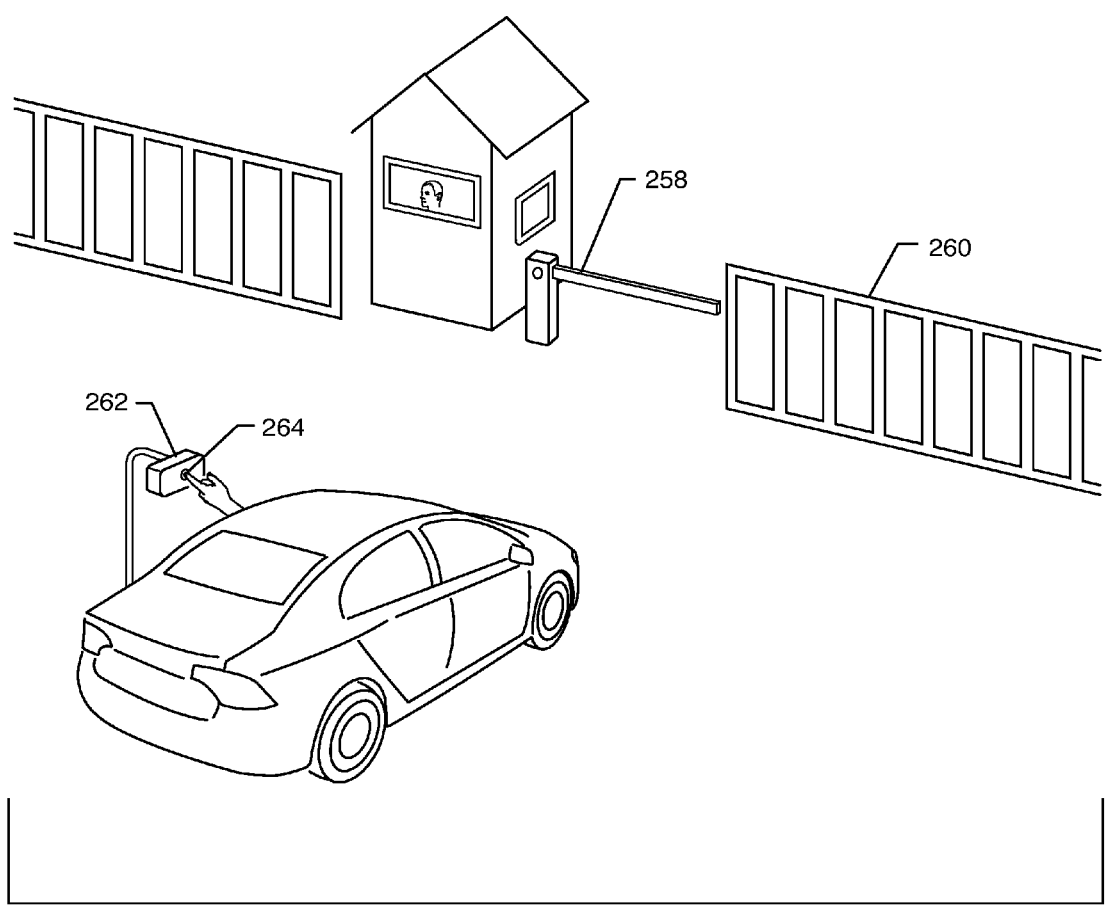
FIG. 42 is a diagrammatic illustration of a vehicle entering into a secured area which is RFID enabled in accordance with the present invention.

FIG. 42 illustrates a guard gate entrance 258 to a high security installation or even a residential subdivision 260. In this case, it is not necessary that the RFID reader system 262 transmit continuously. This provides an additional safety factor for pedestrians walking by that may be pacemaker patients or the like. In this case, the driver of the car drives up (or a pedestrian walks up) and then pushes a push button 264 which activates the RFID reader 262. In this case, a very powerful RFID reader can be used which has a limited transmit time and time-out period of the present invention. As soon as the tag is detected, which can be on the patient, near the patient or on the car then the lift gate is opened. It is not necessary that such a system be manned as shown.

Figure 43:
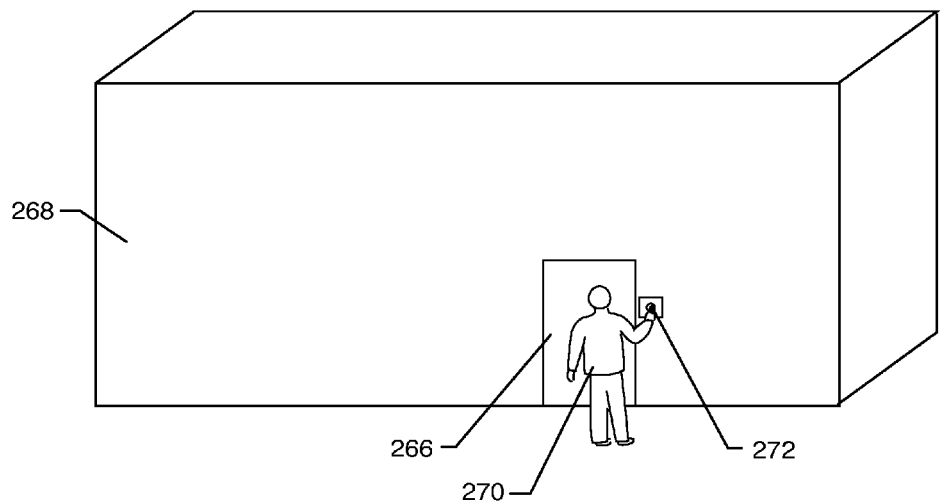
FIG. 43 is a diagrammatic illustration of an individual seeking access to a building having an RFID security system.
Figure 44:
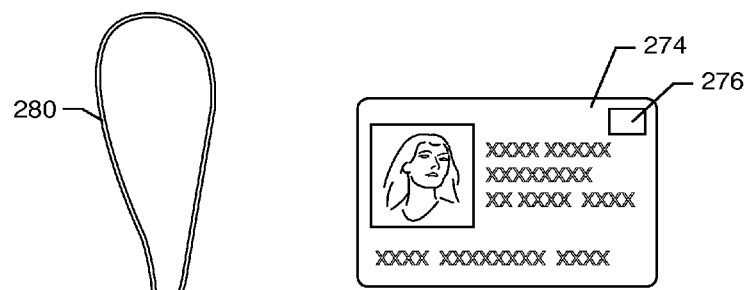
FIG. 44 is an exemplary identification badge incorporating an RFID tag to be read by the security system, which can be placed in one's wallet or purse.
Figure 45:
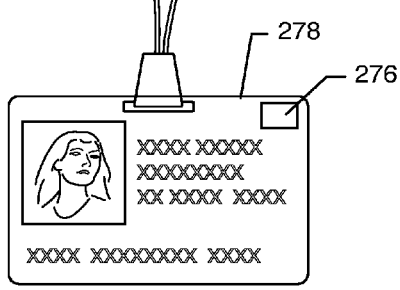
FIG. 45 is another RFID identifying badge, which can be worn around one's neck.
Figure 46:
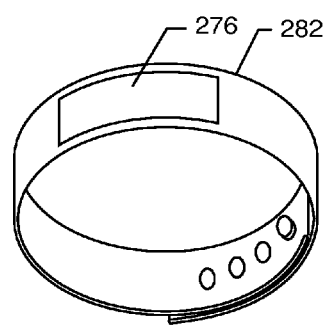
FIG. 46 is a wristband or bracelet which is RFID enabled.

FIG. 43 illustrates a doorway 266 into a high security building 268. Shown is a person 270 possessing an RFID tag (not shown). In a very similar manner to FIG. 42, the person (who may be a pacemaker patient) pushes a button 272 which activates the RFID interrogator transmitter (not shown), which can then detect the RFID tag. The RFID interrogator has a limited transmit time and a time-out period of the present invention. The RFID tag can be on, carried or even embedded within the person. With reference now to FIG. 44, shown is an exemplary identification badge 274, which may include a photograph and identifying indicia thereon, as illustrated, and which has an RFID tag 276 embedded therein or otherwise connected thereto. Such an identification card could be carried in a wallet or purse of the individual 270 in FIG. 43 to gain access to the building 268. FIG. 45 illustrates a similar embodiment of an identification badge 278 which has been modified so as to have a lanyard 280 attached thereto such that the identification badge 278 can be worn around the individual's neck. FIG. 46 illustrates an RFID enabled wristband or watch 282 having an RFID tag 276 associated therewith and which can be used in conjunction with FIG. 43 to gain access to the building 268.

Figure 47:
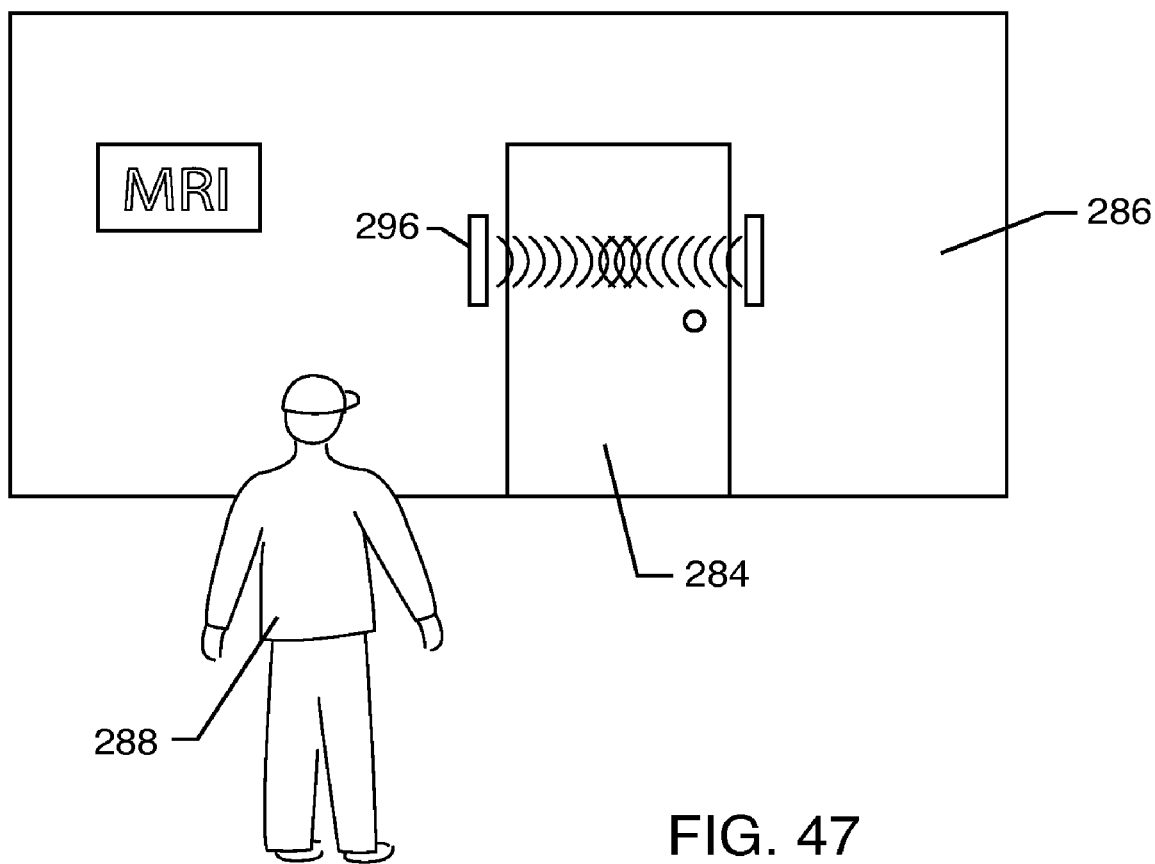
FIG. 47 is a diagrammatic illustration of a patient entering into an imaging facility, and passing through a doorway having RFID communicators in accordance with the present invention which detect the presence of implanted medical devices.

FIG. 47 illustrates the entry 284 to an MRI suite 286. Shown is a patient 288 entering the MRI suite. The patient may have a variety of implants, including a hip implant and a cardiac pacemaker and a coronary stent. It is a feature of the present invention that all of these implanted devices are associated with an RFID tag either associated with each device or in a common location within or on the patient, such as embedded within the patient's wrist or carried by the patient as previously illustrated in FIGS. 44-46. RFID readers embody the limited transmit time and time-out feature of the present invention. When the patient enters through the portal 284 of the MRI suite 286, the MRI technician or radiologist would obtain a read out of all of the implanted devices both active and passive within the patient. It would also be indicated whether these devices were MRI compatible, for example, with a 1.5 Tesla system. This would provide a very high degree of safety. In the past, for example, deep brain stimulator patients have received inadvertent MRI scans which have resulted in serious tissue and brain damage that resulted in serious neurological disorders.

Figures 48, 49:
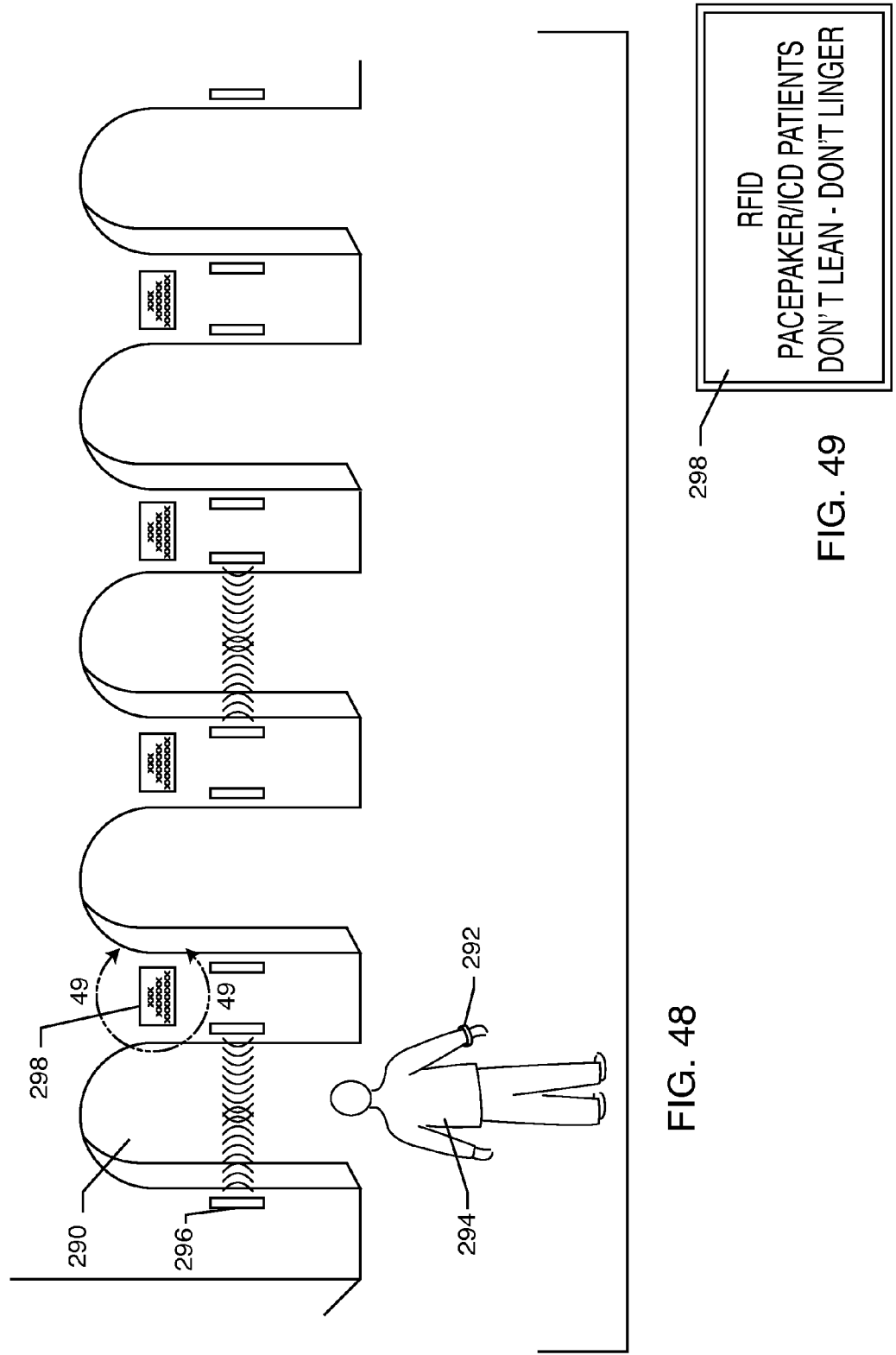
FIG. 48 is a diagrammatic illustration of a plurality of entryway portals flanked by RFID interrogators/readers for permitting entrance into the amusement park or other event.
FIG. 49 is an enlarged view of area "49-49" of FIG. 48, illustrating a sign informing individuals not to linger in the RFID zone as it does not incorporate the present invention.

FIG. 48 is a typical "pinched-down" portal system that is being used in a number of amusement parks across the country. Because RFID readers have a limited read range, instead of having a wide open passage, a number of archways 290 are used, which can still pass a high volume of people traffic. For example, people today may go to amusement parks and obtain an RFID wristband 292 for their child 294. They can then turn their child loose to run all through the park. If the parent wishes to locate their child, all they have to do is go to any convenient kiosk, enter a code and the location of the child will show up on a map of the park. Referring back to FIG. 48, one can see that if there is a large mass of people passing through these portals 290, they will only be inside the portal for a fraction of a second or so as they rapidly pass through this relatively narrow space. Accordingly, the present invention may not be applicable to this type of unique RFID circumstance. Rather, a prior art reader 296 that was continuously transmitting would be required. In this case, signage 298, as illustrated in FIG. 49, would be an appropriate way to warn pacemaker patients to pass through rapidly. The sign would indicate, "Don't lean, don't linger," which is consistent with other techniques that the FDA has used to control electronic articles surveillance gates (EAS gates) when exiting a retail store. FIG. 48 is therefore an illustration that the present invention does not solve all potential Class 1 RFID interactions with pacemakers, but does solve the vast majority of them.

Accordingly, in view of all of the foregoing, it will be appreciated that the present invention relates to design modifications to prior art or newly designed RFID interrogation systems for protecting electronic devices, including medical devices, against RFID-associated electromagnetic interference (EMI). The novel RFID communicators embodied in the present invention include a circuit for limiting the total continuous transmit time of an electromagnetic signal, and a time-out circuit for delaying a subsequent transmission of the electromagnetic signal. By limiting the total continuous transmit time of the electromagnetic signals, in the case of a cardiac pacemaker, only a few heartbeats would be dropped, which is clinically insignificant to the patient. In a preferred embodiment, the total continuous transmit time of the electromagnetic signal is 500 milliseconds or less, and the time-out circuit delays the subsequent transmission of the electromagnetic signal for 2 seconds or more. However, due to the broad applicability of the present invention to various types of transmitters and electronic environments, the total continuous transmit time could be as little as several nanoseconds, and the time-out circuit could delay the subsequent transmission of the electronic signal for up to several minutes or more.

Although several embodiments have been described in detail for purposes of illustration, various modifications may be made without departing from the scope and spirit of the invention. Accordingly, the invention is not to be limited, except as by the appended claims.

What is claimed is:

1. An interrogator for an implantable pulse generator system, the interrogator comprising:

a) a time-out circuit and an actuatable RF signal generator for transmitting an electromagnetic signal,
b) wherein upon first actuation of the RF signal generator, regardless whether an RFID tag is detected, or not, the RF signal generator transmits a first electromagnetic signal having a first limited total continuous transmit time that is no longer than about two heart beats, followed by an interim period of a defined length where the time-out circuit renders the interrogator incapable of transmitting the electromagnetic signal, followed by the RF signal generator transmitting a second electromagnetic signal having a second limited total continuous transmit time that is no longer than about two heart beats,
c) wherein no matter how frequently the RF signal generator is actuated, the time-out circuit prevents the first, second and subsequent transmissions of the electromagnetic signal that are each no longer than about two heart beats after a prior electromagnetic signal has been transmitted from the RF signal generator until the interim period has expired.

2. The interrogator of claim 1, wherein the electromagnetic signal comprises an RFID communication signal.

3. The interrogator of claim 1, wherein the electromagnetic signal comprises an RFID interrogation or tag search signal.

4. The interrogator of claim 1, wherein the electromagnetic signal comprises an RFID test signal.

5. The interrogator of claim 1, wherein the electromagnetic signal comprises an RFID read signal or an RFID write signal.

6. The interrogator of claim 1, wherein the total continuous transmit time of any one of the first, second and subsequent transmissions of the electromagnetic signal is no greater than about five seconds.

7. The interrogator of claim 1, wherein the time-out circuit delays the subsequent transmission of the electromagnetic signal for at least about two seconds.

8. The interrogator of claim 7, wherein the total continuous transmit time of any one of the first, second and subsequent transmissions of the electromagnetic signal is about 500 milliseconds or less.

9. The interrogator of claim 8, wherein the electromagnetic signal comprises an RFID test signal, an RFID tag search signal, an RFID interrogation signal, or an RFID read signal or an RFID write signal.

10. The interrogator The system of claim 1, wherein the electromagnetic signal comprises a modulated signal.

11. The interrogator of claim 1 comprising a read-only or a reader/writer device.

12. The interrogator of claim 1 being in communication with a computer or a computer network.

13. The interrogator of claim 1 or 8 being programmable to actively search for or communicate with an RFID tag.

14. The interrogator of claim 13, wherein the RFID tag comprises a read-only or a readable/writable RFID tag.

15. The interrogator of claim 14 comprising a read-only or a reader/writer device.

16. The interrogator of claim 15 being in communication with a computer or a computer network.

17. The interrogator of claim 1 comprising a portion of an animal or an article tracking system.

18. The interrogator of claim 1, comprising a portion of an electronic article surveillance (EAS) system.

19. The interrogator of claim 18 comprising a check-out station for purchase of goods.

20. The interrogator of claim 19, wherein the check-out station comprises a passageway defining an RFID signal zone in which articles having RFID tags associated therewith are read and means for preventing passageway until all RFID tags are read and the articles paid for.

21. The interrogator of claim 1, wherein the electromagnetic signal is transmitted in the LF or HF frequency range.

22. The interrogator of claim 1 as part of a system comprising:
a) a pulse generator comprising a housing containing a power source electrically connected to control circuitry for generating a pulse of electrical current and delivering the electrical pulse to a lead attachable to the pulse generator for stimulating body tissue contacted by an electrode of the lead; and
b) a radio frequency identification (RFID) tag housed inside the pulse generator housing.

23. An implantable pulse generator system, the system comprising:
a) the pulse generator comprising a housing containing a power source electrically connected to control circuitry for generating a pulse of electrical current and delivering the electrical pulse to a lead attachable to the pulse generator for stimulating body tissue contacted by an electrode of the lead;
b) a radio frequency identification (RFID) tag housed inside the pulse generator housing;
c) an interrogator comprising a time-out circuit for delaying a subsequent transmission of the electromagnetic signal and an actuatable RF signal generator for transmitting an electromagnetic signal,
d) wherein upon first actuation of the RF signal generator, regardless whether an RFID tag is detected, or not, the RF signal generator transmits a first electromagnetic signal having a first limited total continuous transmit time that is no longer than about two heart beats, followed by an interim period of a defined length where the time-out circuit renders the interrogator incapable of transmitting the electromagnetic signal, followed by the RF signal generator transmitting a second electromagnetic signal having a second limited total continuous transmit time that is no longer than about two heart beats,
e) wherein no matter how frequently the RF signal generator is actuated, the time-out circuit prevents the first, second and subsequent transmissions of the electromagnetic signal that are each no longer than about two heart beats after a prior electromagnetic signal has been transmitted from the RF signal generator until the interim period has expired.

24. The implantable pulse generator system of claim 23, wherein the total continuous transmit time of the electromagnetic signal is no greater than about five seconds.

25. The implantable pulse generator system of claim 23, wherein the time-out circuit delays the subsequent transmission of the electromagnetic signal for at least about two seconds.

26. The implantable pulse generator system of claim 25, wherein the total continuous transmit time the electromagnetic signal is about 500 milliseconds or less.

27. The implantable pulse generator system of claim 23, wherein the electromagnetic signal comprises an RFID test signal, an RFID tag search signal, an RFID interrogation, signal, or an RFID read signal, an RFID write signal, or an RFID communication signal.

28. The implantable pulse generator system of claim 23, wherein the electromagnetic signal comprises a modulated signal.

29. The implantable pulse generator system of claim 23, wherein the interrogator comprises a read-only or a reader/writer device.

30. The implantable pulse generator system of claim 23, wherein the interrogator is in communication, with a computer or a computer network.

31. The implantable pulse generator system of claim 23, wherein the interrogator is actively searching for or communicating with an RFID tag.

32. The implantable pulse generator system of claim 31, wherein the RFID tag comprises a read-only or a readable/writable RFID tag.

33. The implantable pulse generator system of claim 32, wherein the interrogator comprises a read-only or a reader/writer device.

34. The implantable pulse generator system of claim 33, wherein the interrogator is in communication with a computer or a computer network.

35. The implantable pulse generator system of claim 31, wherein the RFID tag comprises an antenna and an electronic micro-chip electrically connected to the antenna.

36. The implantable pulse generator system of claim 29, including a barcode reader.

37. The implantable pulse generator system of claim 36, wherein the interrogator writes data received by the barcode reader to an RFID tag.

38. The implantable pulse generator system of claim 37, wherein the data received from the barcode reader is written to permanent memory of the RFID tag.

39. The implantable pulse generator system of claim 38, wherein the interrogator selectively inputs additional data to the RFID tag.

40. The implantable pulse generator system of claim 39, wherein the additional data is written to volatile memory of the RFID tag.

41. The implantable pulse generator system of claim 23 wherein the RFID tag includes retrievable information relating to the active medical device.

42. The implantable pulse generator system of claim 41, wherein the retrievable information includes information pertaining to magnetic resonance imaging (MRI) compatibility of the active medical device or an associated lead system.

43. The implantable pulse generator system of claim 41, including means for changing the retrievable information to correspond to changes in characteristics of the active medical device.

44. The implantable pulse generator system of claim 23 wherein the active medical device comprises any of the following: a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, an endovascular catheter, a Bion or a prosthetic device, and component parts thereof, including lead wires and abandoned leads.

45. The implantable pulse generator system of claim 23 wherein the interrogator comprises a portion of an animal or an article tracking system.

46. The implantable pulse generator system of claim 45, wherein the tracking system comprises a hospital monitoring system.

47. The implantable pulse generator system of claim 46, wherein the hospital monitoring system comprises a patient tracking system, including a plurality of RFID communicators placed in a passageway to create an RFID zone through which the patient is passed.

48. The implantable pulse generator system of claim 46, wherein the hospital monitoring system comprises a medication tracking system.

49. The implantable pulse generator system of claim 48, wherein the medication tracking system comprises at least one RFID interrogator forming an RFID zone through which medication having an RFID tag is passed before being administered to a patient.

50. The implantable pulse generator system of claim 48, wherein the medication tracking system comprises a medication container having an RFID tag or a machine readable code thereon scanned by an interrogator and an RFID or machine readable code associated with the patient also scanned by the interrogator in association with administration of the medication to a patient.

51. The implantable pulse generator system of claim 31, wherein the interrogator comprises a portion of an electronic article surveillance (EAS) system.

52. The implantable pulse generator system of claim 51, wherein the EAS interrogator includes a switch for temporarily actuating the total continuous transient time limiting and time-out circuits when the presence of an active medical device is detected.

53. The implantable pulse generator system of claim 51, wherein the interrogator comprises a check-out station for purchase of goods.

54. The implantable pulse generator system of claim 51, wherein the interrogator of the EAS gate temporarily enters into a limited transmit and timeout period, mode upon sensing an RFID tag associated with a medical device.

55. The implantable pulse generator system of claim 31, wherein the interrogator comprises a portion of an automobile.

56. The implantable pulse generator system of claim 31, wherein the interrogator actively seeks an associated RFID tag.

57. The implantable pulse generator system of claim 56, wherein the interrogator transmits an interrogation signal to the RFID tag when the interrogator senses that the RFID tag is in close proximity.

58. The implantable pulse generator system of claim 56, wherein the interrogator comprises an automated vehicle entry, security or vehicle start system.

59. The implantable pulse generator system of claim 31, wherein the interrogator electromagnetic signal comprises an LF or HF frequency signal.

* * * * *

UNITED STATES PATENT AND TRADEMARK OFFICE
CERTIFICATE OF CORRECTION

| | | |
|---|---|---|
| PATENT NO. | : 8,115,600 B2 | Page 1 of 1 |
| APPLICATION NO. | : 12/566490 | |
| DATED | : February 14, 2012 | |
| INVENTOR(S) | : Robert A. Stevenson, Geddes Frank Owen Tyers and Christine A. Frysz | |

It is certified that error appears in the above-identified patent and that said Letters Patent is hereby corrected as shown below:

Column 25, line 46 "The interrogator The system of claim 1," should be "The interrogator of claim 1,"

Signed and Sealed this
Second Day of October, 2012

David J. Kappos
*Director of the United States Patent and Trademark Office*